US009114252B2

(12) United States Patent
Yu et al.

(10) Patent No.: US 9,114,252 B2
(45) Date of Patent: Aug. 25, 2015

(54) IMAGE-GUIDED THERAPY DELIVERY AND DIAGNOSTIC NEEDLE SYSTEM

(75) Inventors: Yan Yu, Philadelphia, PA (US); Wan Sing Ng, Singapore (SG); Tarun Podder, Cherry Hill, NJ (US); Lydia Liao, Philadelphia, PA (US); Yongde Zhang, New York, NY (US)

(73) Assignee: University of Rochester, Rochester, NY (US)

( * ) Notice: Subject to any disclaimer, the term of this patent is extended or adjusted under 35 U.S.C. 154(b) by 1096 days.

(21) Appl. No.: 12/095,824

(22) PCT Filed: Dec. 4, 2006

(86) PCT No.: PCT/US2006/046101
§ 371 (c)(1),
(2), (4) Date: Sep. 24, 2009

(87) PCT Pub. No.: WO2007/064937
PCT Pub. Date: Jun. 7, 2007

(65) Prior Publication Data
US 2010/0036245 A1 Feb. 11, 2010

Related U.S. Application Data

(60) Provisional application No. 60/741,468, filed on Dec. 2, 2005, provisional application No. 60/818,329, filed on Jul. 5, 2006.

(51) Int. Cl.
*A61B 8/00* (2006.01)
*A61N 5/10* (2006.01)
(Continued)

(52) U.S. Cl.
CPC ........... *A61N 5/1027* (2013.01); *A61B 10/0233* (2013.01); *A61B 2010/0208* (2013.01); *A61B 2019/464* (2013.01); *A61N 2005/1011* (2013.01)

(58) Field of Classification Search
CPC ..................... A61N 5/1027; A61N 2005/1011; A61B 10/0233; A61B 2010/0208; A61B 2019/464
See application file for complete search history.

(56) References Cited

U.S. PATENT DOCUMENTS 2,304,161 A * 12/1942 Froehlich et al. ........... 123/41 R
2,603,145 A *  7/1952 Dreis ............................. 100/46
(Continued)

FOREIGN PATENT DOCUMENTS

JP        2000-294991    * 10/2000   ............. H05K 13/04

OTHER PUBLICATIONS

Strang et al., Real-Time US versus CT Determination of Pubic Arch Interference for Brachytherapy, Radiology 2001; 219:387-393.*
(Continued)

*Primary Examiner* — Bo J Peng
(74) *Attorney, Agent, or Firm* — Cooper & Dunham LLP

(57) ABSTRACT

An automated system for delivery of seeds or other therapeutic or diagnostic capsules to internal organs of the patient's body for radiation brachytherapy includes a needling mechanism, a 2DOF robot, an ultrasound probe driver, a 5DOF passive platform, and an easy lock cart. The needling mechanism implants radioisotope seeds by its cannula and stylet driven by two moving stages pushed by DC motors with ball screw transmission. Force sensors are included for detecting insertion forces and bending force. In another embodiment, the needle is rotated for insertion into the patient and can also be used for tissue removal for biopsy. The two embodiments are usable together or separately.

98 Claims, 29 Drawing Sheets

(51) Int. Cl.
*A61B 10/02* (2006.01)
*A61B 19/00* (2006.01)

(56) References Cited

U.S. PATENT DOCUMENTS

| | | | | |
|---|---|---|---|---|
| 2,892,542 | A * | 6/1959 | Broido | 209/554 |
| 3,529,480 | A * | 9/1970 | Kaspareck | 74/63 |
| 4,002,169 | A * | 1/1977 | Cupler, II | 604/22 |
| 4,393,965 | A * | 7/1983 | Zouzoulas | 192/48.91 |
| 5,503,024 | A * | 4/1996 | Bechtel et al. | 73/852 |
| 5,514,071 | A * | 5/1996 | Sielaff et al. | 600/3 |
| 5,931,786 | A * | 8/1999 | Whitmore et al. | 600/459 |
| 5,961,527 | A * | 10/1999 | Whitmore et al. | 606/130 |
| 6,099,457 | A * | 8/2000 | Good | 600/8 |
| 6,126,607 | A * | 10/2000 | Whitmore et al. | 600/459 |
| 6,129,670 | A | 10/2000 | Burdette et al. | |
| 6,223,864 | B1 * | 5/2001 | Phelps et al. | 188/19 |
| 6,273,862 | B1 | 8/2001 | Privitera et al. | |
| 6,572,526 | B1 * | 6/2003 | Ford | 600/7 |
| 6,689,072 | B2 | 2/2004 | Kaplan et al. | |
| 6,752,753 | B1 * | 6/2004 | Hoskins et al. | 600/7 |
| 6,869,390 | B2 | 3/2005 | Elliott et al. | |
| 2002/0035321 | A1 * | 3/2002 | Bucholz et al. | 600/407 |
| 2002/0143269 | A1 * | 10/2002 | Neuenfeldt | 600/564 |
| 2003/0018232 | A1 * | 1/2003 | Elliott et al. | 600/1 |
| 2003/0078495 | A1 * | 4/2003 | Goodwin | 600/424 |
| 2004/0147800 | A1 * | 7/2004 | Barber et al. | 600/7 |
| 2004/0204646 | A1 | 10/2004 | Nagler et al. | |
| 2005/0015010 | A1 * | 1/2005 | Antich et al. | 600/449 |
| 2005/0185196 | A1 * | 8/2005 | Kitamura et al. | 356/614 |
| 2005/0209499 | A1 * | 9/2005 | Elliott et al. | 600/1 |

OTHER PUBLICATIONS

Taschereau et al., Seed misplacement and stabilizing needles in transperineal permanent prostate implants, Radiotherapy and Oncology 55 (2000) 59-63.*

* cited by examiner

IMAGE-GUIDED THERAPY DELIVERY AND DIAGNOSTIC NEEDLE SYSTEM

REFERENCE TO RELATED APPLICATIONS

The present application is a National Phase of PCT/US2006/046101, filed Dec. 4, 2006, which claims the benefit of U.S. Provisional Patent Application No. 60/741,468, filed Dec. 2, 2005, and of U.S. Provisional Patent Application No. 60/818,329, filed Jul. 5, 2006, whose disclosures are hereby incorporated by reference in their entireties into the present disclosure.

STATEMENT OF GOVERNMENT INTEREST

The work leading to the present invention was supported in part by the National Cancer Institute under Grant No. R01 CA091763 and Grant No. R33 CA107860. The government has certain rights in the invention.

FIELD OF THE INVENTION

The present invention relates generally to the field of devices used in the radiation treatment instruments. More specifically, the present invention relates to the automated seed delivery system of radiation therapy, for example, the brachytherapy of low dose radiation treatment of prostate cancer. The present invention also relates generally to the field of diagnosis and therapy by tissue removal, for example, core biopsy and interstitial lumpectomy of breast cancer. Another specific field that the present invention relates to is the use of real-time sensors for detecting focal regions of cancer in soft tissues such as the prostate and breast.

BACKGROUND OF THE INVENTION

Prostate cancer is the second leading cause of death for men after lung cancer. Over 90% of prostate cancer goes undetected until it is untreatable and has spread to the bone and lymphatic system. Each year, over 400,000 men in the United States alone undergo prostate surgery, and over a billion dollars a year is spent on prostate treatment. More than 230,000 men are diagnosed with prostate cancer and 30,000 men die from it each year. The treatments for prostate cancer include mainly complete surgical removal and radiation therapy. Currently, the most popular treatment is complete removal of the prostate by means of a surgical procedure. However, like other surgeries, such a procedure is invasive and with wounds, and the patient needs a long recovery time, and especially, such surgery often results in side effects, such as incontinence and impotence.

Radiation therapy generally comprised of external radiation therapy and internal radiation brachytherapy. External radiation therapy is seldom used currently because of its excessive irradiation to other organs and tissues other than the prostate gland. Radiation brachytherapy is well known and is becoming a broadly acceptable treatment method. There are two types of brachytherapy: high dose radioisotope and low dose radioisotope. In the former manner, a catheter and an after loader are used, and the high dose radioisotope is transferred to the desired location by a wire with the catheter. The radiation stays in the patient's body for a relatively short time. In the latter manner, a number of radiation seeds are implanted into the patient's body by an array of hollow needles through which the seeds will pass; the seeds will be deposited into a pre-planned positions determined by the physician, so that an ideal irradiation assignment in the prostate gland can be acquired.

Low dose radioisotope brachytherapy has the advantages of minimally invasive treatment, low cost, low side effects, and keeping the prostate, which will increase the patient's self confidence. The most commonly used method for seed delivery into the prostate is by an array of hollow needles with stylet needles which are inserted into the patient's body guided by a template with regular interval chambers. The hollow needles retract from the prostate, and the stylet needles stay there; then the seeds are deposited in the predetermined locations. The whole process of seed implanting is under monitoring of a ultrasound probe. The current locations of needles and seeds are detected immediately, so that the necessary adjustment can be done to obtain an ideal seeds position accuracy. The final accuracy and effectiveness of low dose brachytherapy is greatly related to the ultrasound probe's position and motion accuracy.

Radioactive seed delivery and implantation into some organs of the patient is a common procedure in radiation brachytherapy, for instance, low dose brachytherapy to prostate cancer. Such seeds commonly are made of Palladium-103 or Iodine-125. A plurality of such tiny seeds are delivered into the body arranged in and surrounding the tumor obtaining required local irradiation and has as low as possible effect to other normal tissue.

Traditionally, the seed delivery procedure is commonly achieved by inserting a cannula which is a hollow needle into the body first, to make the needle tip reach the required location of the seed implantation. A stylet will push the seeds passing through the cannula until the seed drop from the cannula tip by which one seed will be implanted by this process. More seeds will be implanted while the cannula continues retracting and the stylet stays there. Currently, the seed implantation process is achieved by manual techniques assisted by a very simple device, which comprises a template with a plurality of guiding holes for needle insertion of the cannula and the stylet. An applicator for grade seed delivery and stylet positioning is broadly used in current art which requires operator's skillful manual operation; otherwise, a wrong number and wrong position of seeds maybe implanted, and seeds may drop. Such process is commonly guided by transrectal ultrasound image or by MRI.

U.S. Pat. No. 5,938,583 describes a combined precise implant needles and method, comprising an insertion stylet, a sleeve element which has a larger diameter than the stylet, and a needle in which radioactive seeds have been preloaded for implanting.

U.S. Pat. No. 6,311,084 shows a computer based method and apparatus for providing prostate brachytherapy using Interventional Magnetic Resonance Imaging. The invention allows a treatment plan to be developed and the implantation procedure to be performed initially in accordance with the developed treatment plan. Modification to the plan is made in real-time by the invention software module coupled to the IMR imaging system. In this system, all the operation of this invention is still done by manual way.

U.S. Pat. No. 6,796,935 introduces a seed implantation apparatus which can perform multiple seed implantation with its plurality of hollow needles, which can hold one more radioactive seeds. This apparatus also includes pistons for each of the hollow needles and a plate located behind the pistons with a rod and a mechanical trigger, wherein the actuation causes the plate to move the pistons into said needles. This invention's advantage is that it can deliver plurality of seeds in the same time, so that increase the efficiency.

U.S. Pat. No. 5,860,909 describes an applicator for implanting seeds at variably spaced locations in a patient's body. The apparatus includes a needle inserted into the body, a base member adapted to be maintained generally stationary with respect to a surface of the body during use, and a needle chuck, which is slidably mounted with respect to the base member, for releasably coupling the needle. The apparatus also includes a seed magazine mounted on the needle chuck for dispensing seeds into the needle bore, a stylet extendable through the needle bore for forcing seeds in the bore into the patient's body, and a barrel attached to the needle chuck. This invention is currently mostly used in many hospitals for prostate brachytherapy, but it is still manual operation, the operator has to do his tedious job carefully.

U.S. Pat. No. 6,869,390 describes an automated implantation system for radioisotope seeds, this invention is the latest development achievement in this field, in which a very complicated seed cartridge and a gantry type for supporting the needling mechanism are used. There are still many disadvantages of this system, a long time is needed for a practical and commercial product is obtained.

Concerning the ultrasound probe driving device, U.S. Pat. No. 5,931,786 describes a manual driving device to ultrasound probe or the same; gear racks are used to obtain the probe's forward and backward translational motion, which is driven by a hand knob. The template is located in the end of the support close to the patient body. Scale is also made in the side of guide rods for easy observation of the travel distance.

U.S. Pat. No. 5,871,448 introduces a stepper apparatus for use in the imaging/treatment of internal organs using an ultrasound probe. This apparatus includes a body portion, a support element for holding the ultrasound probe, a slide portion for moving the support element for holding the template. The ultrasound probe can be moved longitudinally. Rack and gear arrangement are used and dual motion of indexed and continuous motions can be achieved.

The above two inventions are commonly used apparatus for support and driving ultrasound probe now. But they have only translation motion, not suitable for sagittal scanning. There is a need to develop a multi-functional, easy operating, more accurate ultrasound probe driver which is integrated with the needling mechanism, an initial positioning passive platform and a supporting cart.

Seed implantation is tedious and costs much operating room time with low efficiency and low accuracy in current art. There is no a practical system obtained. It is necessary to develop an automated and ultrasound guided seed delivery system with more practical advantages including high efficiency and high accuracy.

Accurate intervention of surgical needles is very important in various medical diagnostic and therapeutic procedures like tissue biopsy, brachytherapy, anaesthesia, vaccinations, blood/fluid sampling, abscess drainage, catheter insertion, cryogenic ablation, electrolytic ablation, neurosurgery, deep brain biopsy, etc. Precise placement of needles in soft tissue is challenging because of several reasons such as tissue heterogeneity and elastic stiffness, tissue deformation and movement, unfavorable anatomic structures, needle bending, inadequate sensing, and poor maneuverability. Some of the factors such as needle bending, tissue deformation and movement are directly related to the force experienced by the needle during insertion. A portion of these forces and deformations depend on the needle geometry and insertion techniques. Therefore, understanding of the complex mechanism of needle interaction with soft tissue is an active research area.

Currently available breast or other biopsy devices rely on manual insertion of large gauge needles into the patient's tissue. Typically, a biopsy needle with a stylet is inserted into the abnormal tissue, under the guidance of an imaging modality, such as ultrasound or magnetic resonance imaging ("MRI"). The stylet is then removed. A syringe is attached to the needle, suction is applied through the syringe and then the needle is manually thrust into and out of the tissue to capture and remove cellular material. However, rather than cutting the tissue to enable collection in the needle bore, the thin needle tends to displace the tissue, especially rigid malignant tissue. Therefore, only a small number of cells may be obtained. Even after repeated attempts, a sufficient amount of tissue might not be obtained. Displacement of tissue also alters the frame of reference defined by the imaging modality.

To improve yield, larger bore needles have been used. However, the risk of damage to the tissues that the needle has to traverse to reach the area of pathology, as well as the risks of bleeding, infection and patient discomfort, rise with increasing needle thickness. Healing time may therefore be increased. Large needle core biopsy needles may also cause significant damage to certain organs, such as the lungs and the spleen. As with fine needles, displacement of movable tissues, such as breast tissue, is also a problem.

Significant tissue/organ deformation and movement (both translational and rotational) are observed during puncturing capsule of inner organs like prostate, liver, etc. or skin of external organs like breast, etc. These undesired deformation and movement can cause deflection of the needle and the target resulting in clinical complications such as vital tissue damage, misdiagnosis, under/over dosing with radiation, tumor seeding, etc. Although the biological tissue relaxes and regains the position partially, there are some organ rotation and deformation which do not recover during surgery and consequently the whole surgical plan becomes erroneous. Therefore, there remains a need for a biopsy need that substantially reduces needle puncturing force and tissue deformation, while improving targeting accuracy.

As diagnostic markers and tools become increasingly sophisticated, smaller and smaller cancers are detected in their earliest stages, confined to such organs as the breast. The traditional method for removing such cancers is open surgery. Surgery causes trauma to the patient, is often performed without real-time image guidance, and may result in unnecessary removal of healthy tissue and/or geographic miss of cancer. A certain number of less invasive, ablation techniques exist, including heating by radio-frequency (RF), ultrasound and laser. A common drawback across all these ablation techniques is that tissue cannot be removed from the body in its natural biological state for subsequent histological examination. Particularly, pathological status of the margin around the ablation is difficult to determine due to burning, making subsequent oncological management of the patient very uncertain. There remains a need to excise tissue without such difficulties.

SUMMARY OF THE INVENTION

It is an object of the invention to meet the above-noted needs.

One embodiment of the invention is directed to an automated system for radioisotope seeds delivery to internal organs of the patient's body for radiation brachytherapy. This system comprises a needling mechanism, a 2DOF robot, an ultrasound probe driver, a 5DOF passive platform, and an easy lock cart.

The needling mechanism which is supported by the 2DOF robot achieves the final delivery to the patient's body. The needling mechanism includes a cannula moving stage driving the cannula which is a hollow needle for puncturing the tissue, a stylet moving stage driving the stylet which pushes the radioisotope seeds passing through the cartridge, three DC motors among which two drive ball screws and one drives the cannula to obtain its rotation while inserting by gear transmission, two z-direction force sensors installed in the back ends of the cannula and the stylet, one x-y direction force sensor detecting the bending force of the cannula.

Encoders are included with the two translation drive motors. Two z-direction force sensors are installed in the back end of the stylet and cannula for detecting the inserting force along axial direction of the stylet and cannula, and one x-y force sensor is installed in the front support end for detecting the cannula's side force for bending tendency. The sensors extend the device's application, for instance, a closed-loop automatic control system or emergency case hint, such as needle hitting the bone.

A specially designed seed cartridge holder is also included which is compatible with commercial seed cartridge with easy loading and unloading function by the positioning plunger and tightening knob. Easy loading and unloading structure for needles including stylet and cannula, and for sterilizers in the component interference places are also included in this device. The device has compact design for the motion transmission moving stages in which ball screws are also used as bushing shaft for supporting.

The ultrasound probe driver achieves ultrasound probe's gripping, and motions of translation and rotation by which translational scanning and sagittal scanning are obtained. The ultrasound images provide 3D construction information of the patient's organ, and other operation, for example, irradiation planning, needle inserting of the procedure will be based on this information. The ultrasound probe driver includes two motors, two clutches, two encoders, one ball screw, one ball spline, gear transmissions, a half-ring bearing, a gripper, knobs, etc., with motorized and manual ways. Two manual stabilization needle guides with two rotation adjustment functions are installed in the front location close to the patient, by which two stabilization needles can be guided and fixed for the stabilizing the organ for other needle's accurate inserting and the seeds' implantation.

In the area of probe clamp, a half-ring is designed supporting and implementing rotation of the probe, the motion transmission to the half bearing is by two spur gears from the ball spline. The half-ring design is advantageous in the operation of installing the probe into the clamp because its "open" structure. A reverse directional thread drive screw is used in the probe clamp, for realizing the probe's clipping and releasing. This design not only can ensure the probe's center line position accuracy, but also has the function of self-lock which is the most important feature for a "clamp".

Two hand knobs are installed in both ends of the tightening screw, which ensure the ease to access the knobs.

An optional support frame is arranged in the front end of the mechanism in the side which is close to the patient. The prostate brachytherapy needle guidance template is supported by this frame for this application, and two guidance structures which are arrangement just below the template in both lateral sides are included also in the frame. Theses two guidance structure are used for guiding the stabilization needles to the prostate before prostate brachytherapy.

Two guide rods are used to guide and support the clamp and the moving stage which is a great help to make the mechanism light and compact.

This ultrasound probe driving device can be used as either an automatic or manual diagnostic scanning, or a biopsy or brachytherapy guiding to prostate or other possible organs.

A 2DOF (two degrees of freedom) robot achieves the function of positioning motions along up-down and left-right directions of the needling mechanism. Guide rails which are driven by ball screws connected to DC motors are used, and a hanging up pattern of structure for the supporting has more access space to the ultrasound probe and its gripper. An angulations and manual take over structure is used in the connection location between the 2DOF robot and the needling mechanism, which provides ±5° angulations to the needling mechanism to make possible oblique insertion of needles for avoiding pubic arch and manual way replacement under emergency case of the system failure.

The 2DOF robot and the ultrasound probe driver are mounted on one support component which is supported by the 5DOF (five degrees of freedom) passive platform. The 5DOF passive platform can achieve the upper part's up-down, left-right, forward-backward, pitch and yaw motions, which act as the initial positioning and posturing of the ultrasound probe and the needling mechanism. The five joints utilize worm gear transmission and lead screw transmission with self-lock function.

Below the other four parts are the cart supporting the whole system's weight and moving it with easy locking pedal controlled by link mechanism acting on four corners by which a stable support are obtained.

The objects of the invention are:

1) To provide a radioactive seed delivery device with its cannula and stylet driven by two DC motors, ball screws and two moving stages respectively.

2) To provide an accurate seed delivery function by accurate needle insertion targeting with cannula rotation driven by a separate DC motor with spur gearing.

3) To provide a compact and motorized delivery device, in which encoders for detection motor motion status, two z-direction and one x-y force sensors for detecting needle insertion force and bending force are installed in stylet and cannula. These features are good advantages while constructing an automatic closed-loop control system and emergency case treatment.

4) To provide a supporting and driving device to the ultrasound probe for transrectal prostate scanning or prostate brachytherapy. This device can drive the ultrasound probe translational motion and rotational motion in both motorized and manual modes.

5) To provide an open, easy operation probe clamp with self-lock function by half-ring bearing and reverse-directional thread tightening screw.

6) To provide a compact and easy operational method for stabilization needle guidance of prostate brachytherapy. The guidance structure can provide two degree of freedom adjustment motions to the stabilization needles.

The automated system for radioisotope seeds delivery to internal organs of the patient's body for radiation brachytherapy is disclosed. The whole system comprises a needling mechanism, a 2DOF robot, an ultrasound probe driver, a 5DOF passive platform, and an easy lock cart.

The needling mechanism implants radioisotope seeds by its cannula and stylet driven by two moving stages pushed by DC motors with ball screw transmission. Force sensors are included for detecting insertion forces and bending force. These force sensors provide ability for automated closed-loop control.

The needling mechanism can move along left-right and up-down directions driven by the 2DOF robot which includes two linear motions driven by motors and transmitted by guide rails and ball screws.

There is an angulations and manual take over structure in the location connecting the needling mechanism and 2DOF robot, which provides ±5° angulations to the needling mechanism to make possible oblique insertion of needles for avoiding the interference with pubic arch and manual way replacement under emergency case of the system failure.

The ultrasound probe driver has motorized and manual options for driving and has translational scanning and sagittal scanning patterns. A half-ring bearing and open style gripper allow the easy access possible of ultrasound probe while mounting it to the machine. Two stabilization needle guide structures are included also in the probe driver, to assist and fix the stabilization needles to the organ before implantation.

The 2DOF robot and the ultrasound probe driver are mounted on a support component which is supported by the 5DOF passive platform with up-down, left-right, forward-backward, pitch and yaw motions for the initial positioning and posturing of the ultrasound probe and the needling mechanism.

A cart supporting and moving the whole system is included also.

Another embodiment of the invention, usable with the first, relates to a biopsy or brachytherapy needle that substantially reduces needle puncturing force and tissue deformation, while improving targeting accuracy. The needle of the present invention is rotatable around its longitudinal axis by command of the person performing the needle (user). The needle is preferably housed in a housing that contains a motor. The motor drives the rotation of the needle, preferably through a gearing system that can increase or decrease the rotational speed of the needle at the choosing of the user. The motor can be activated by the user by activating a switch located on the housing. Preferably, the switch is conveniently located on the housing such that the user can activate the switch with minimal force and minimal distraction while inserting the needle into a patient. Typically the switch is a button operable by the user by depressing the button with his/her thumb. The biopsy of the present invention is operable with currently available biopsy needles, including, but are not limited to, diamond tip and bevel tip brachytherapy needles and Mammotome® and Vacora™ breast biopsy needles. Although the present invention discloses biopsy or brachytherapy needles, the principle of the present invention can be used for other needles where reduction of needle puncturing force and tissue deformation, and/or improvement in targeting accuracy are desired. The second preferred embodiment addresses the need for a method and system to excise tissue through a percutaneous needle core in a systematic "peeling" fashion, resulting in retrieval of "shells" of tissue surrounding a mass with preservation of histological characteristics.

Insertion of large-core surgical needles into soft tissue is associated with large deformation of the tissue and with high insertion force and target deflection. Several breast biopsy devices rely on manual insertion of large-gauge needles into the tissue. The second preferred embodiment permits easy entry by needle rotation and oscillation, where the operator controls the speed of rotation by the press of a button without the need for a second hand.

During biopsy, the physician sometimes has to rotate the needle/gun manually to achieve the effect of drilling through dense or otherwise hard tissue before reaching the target area. The motorized rotation of the second preferred embodiment achieves the same or better effect through a simple, one-finger operation, decreases the time for biopsy, increases the accuracy of the biopsy, and decreases the chance of complications.

To advance a large-gauge needle (10 Ga to 8 Ga) into deep tissue such as the breast manually, considerable force and effort are required on the part of the operating physician. During clinical practice, the inventors have learned that rotation or rotational oscillation of the needle/gun device by the hand eases entry and advance of the needle into tissue. That is described in T. K. Podder et al, "Assessment of prostate brachytherapy and breast biopsy needle insertions and methods to improve accuracy," presented and published at the ICBME, Singapore, 7-10 Dec. 2005, whose disclosure is hereby incorporated by reference in its entirety into the present disclosure. However, placement of large-gauge needles deep into tissue is a clinically challenging skill; to add the need for manual rotation or oscillation while advancing the needle is physically too demanding and may introduce imprecision into the procedure.

The second preferred embodiment provides a motorized needle rotation mechanism into the biopsy gun assembly, which is controlled by a button situated within reach of the physician's thumb while holding the biopsy gun. The button is not only a switch to actuate the motorized rotation and/or oscillation mechanism but also a graduated control for the speed of rotation as well as a toggle between full rotation and CW-CCW oscillation of the needle about its axis.

Either the cannula or the stylet can be rotated independently, or the cannula and stylet can be rotated together. The velocity can be modulated during needle insertion into tissue.

The motorized needle rotation of the second embodiment permits controlled, systematic positioning of the cutting area of the needle in both orientation and depth. Continuous activation of the said motorized mechanisms will result in a "peeling" motion, the extent and shape of which can be controlled by the operating clinician.

BRIEF DESCRIPTION OF THE DRAWINGS

Two preferred embodiments of the invention will be set forth below with reference to the drawings, in which.

DETAILED DESCRIPTION OF THE PREFERRED EMBODIMENTS

Figure 1:
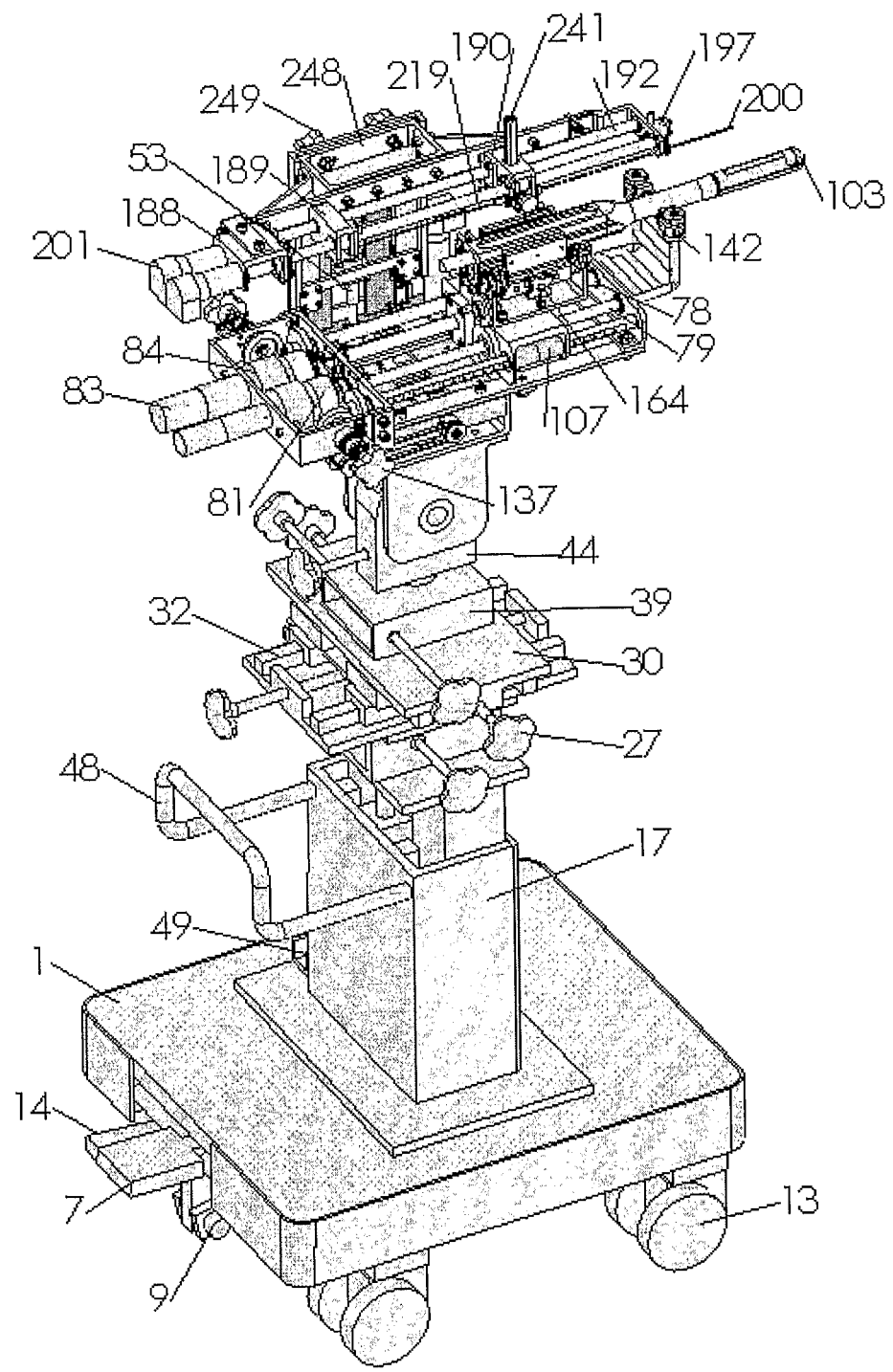
FIG. 1 is a perspective view of the whole seed delivery system according to the first preferred embodiment. All the five models are shown including the needling mechanism, the 2DOF robot, the ultrasound probe driver, the 5DOF passive platform and the cart.
Figure 2:
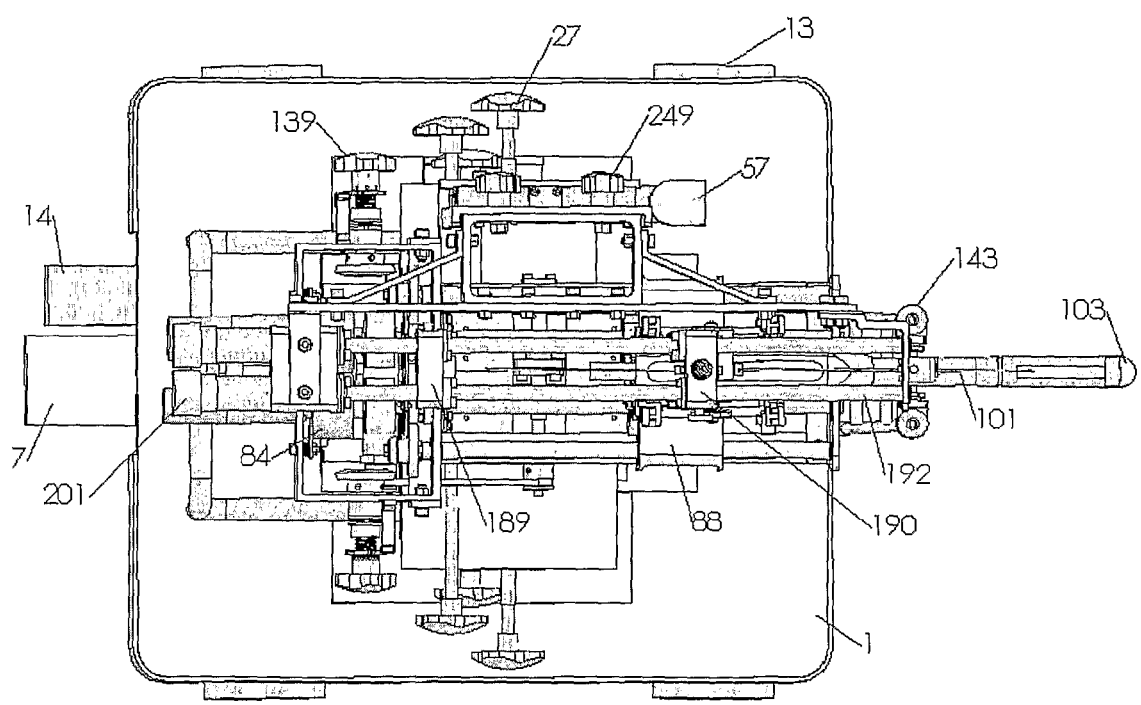
FIG. 2 to FIG. 4 are a top view, side view and back view of the 3D assembly of the whole seed delivery system.
Figure 3:
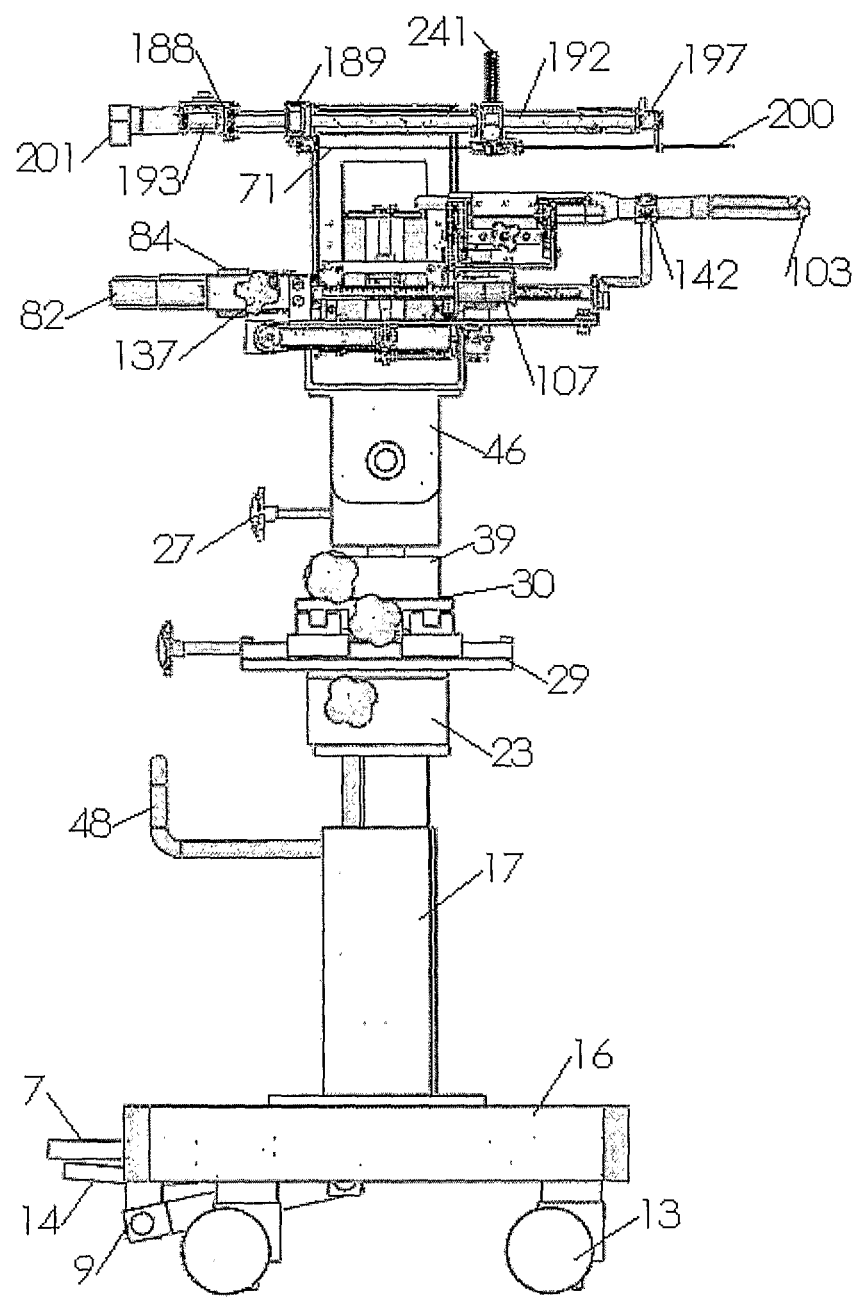
Figure 4:
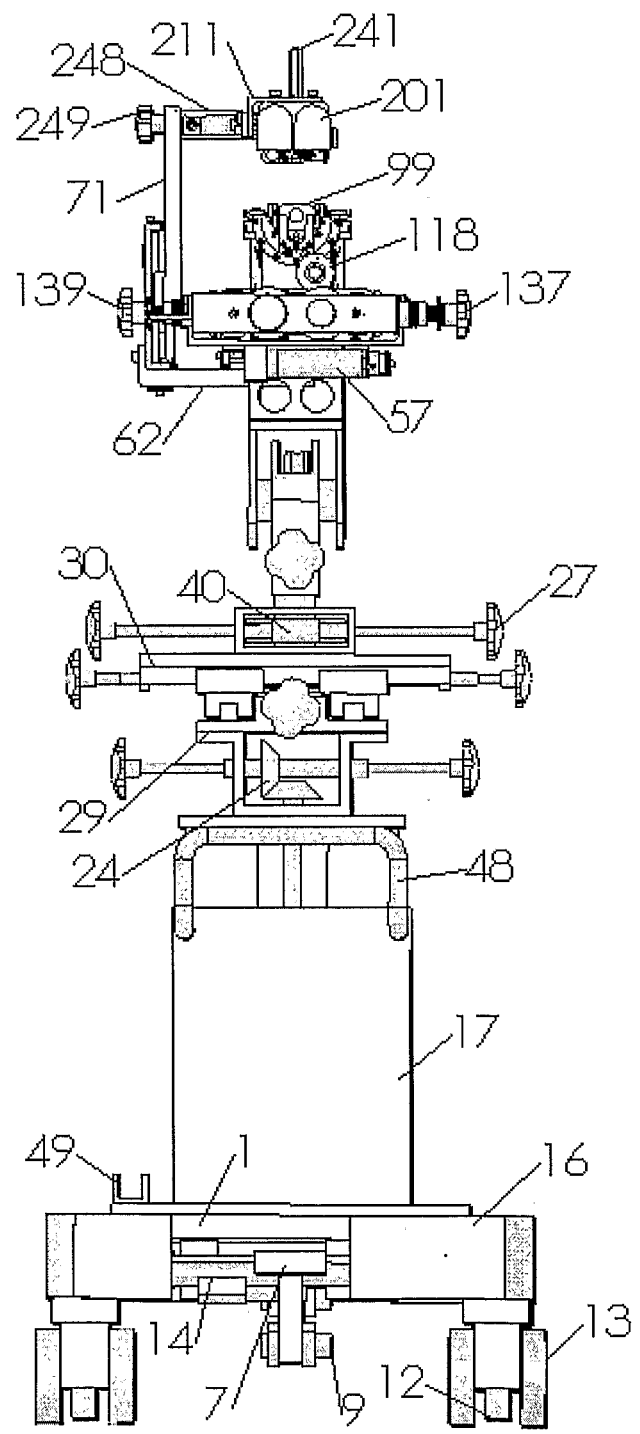

Preferred embodiments of the invention will be set forth in detail with reference to the drawings, in which like reference numerals refer to like elements throughout.

FIG. 1 to FIG. 4 show the perspective view, top view, side view and back view of 3D assembly of the first preferred embodiment, in which radioisotope seeds are delivered into the patient's body for tumor treatment, for instance, prostate cancer low dose brachytherapy. All the five models are shown including needling mechanism 201, 2DOF robot 53, ultrasound probe driver 83, 5DOF passive platform 32 and the cart 1.

There are a total of seven DC motors in the system, to obtain cannula insertion with rotation, stylet movement for pushing the seeds into the cannula and implanting in the body, the needling mechanism's left-right and up-down motions for positioning along x and y axis, ultrasound probe's translation and rotation for translational scan and sagittal scan.

There are a total of three force sensors included, for force detection of cannula and stylet, and cannula bending force detection while inserting.

The features of this system are as below.
 a. All the motions are motorized, and encoders and force sensors are used to guarantee an automated system can be realized easily;
 b. Inserting with needle rotation, to reduce the friction force between the needle and the tissue, and to improve the targeting to the required location of the body;
 c. Needle insertion force and bending force can be detected by force sensors for monitoring the working status, by which closed-loop control function of the whole system can be realized;
 d. The needle position can be adjusted along x and y directions to obtain a required insertion area in the perineum wall or other body location;
 e. Needling mechanism angulations structure for ±5° adjustment to needles;
 f. Manual take over structure of the needling mechanism in case of system failure;
 g. Hang up pattern of the 3DOF grantry for larger access space to ultrasound probe driver and needling mechanism;
 h. Manual operation option for ultrasound probe driver;
 i. Two scanning patterns of translational and sagittal for ultrasound probe driver are included;
 j. A pair of half ring bearings and reverse directional thread tightening shaft for the probe gripper are designed for ultrasound probe's easy access while attaching;
 k. Two stabilization needle guides are included which has two DOF rotations to the guide holes, this ensures the function of stabilization needle guidance and fixture;
 l. Commercial seed cartridges are compatible;
 m. 5DOF passive platform achieves the initial adjustments and positioning of the upper three models.
 n. Easy lock cart supports the whole system and guarantee its stability.
 o. Easy loading and unloading structure with stylet and cannula needles;
 p. Compact design;
 q. Easy loading and unloading structures for sterilizers in the places where they are necessary;
 r. Special design cartridge holder for easy installation and taken off to the commercial cartridge;
 s. Special design cannula head shown by FIG. 16 for convenient loading and unloading;
 t. High efficiency of needle insertion and seed implantation.

Figure 5:
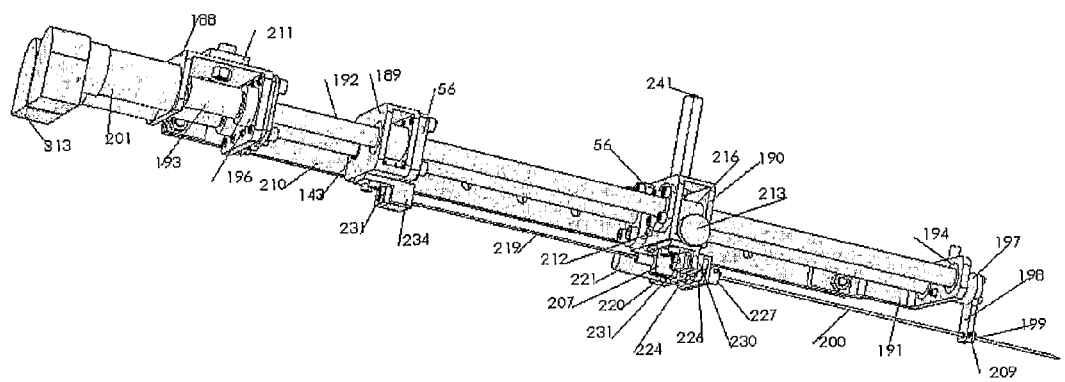
FIG. 5 is a perspective view of the needling mechanism. All the main parts of this mechanism are shown, for example, motors, encoders, couplings, ball screws, two moving stages, stylet and cannula, front support, etc.
Figure 6:
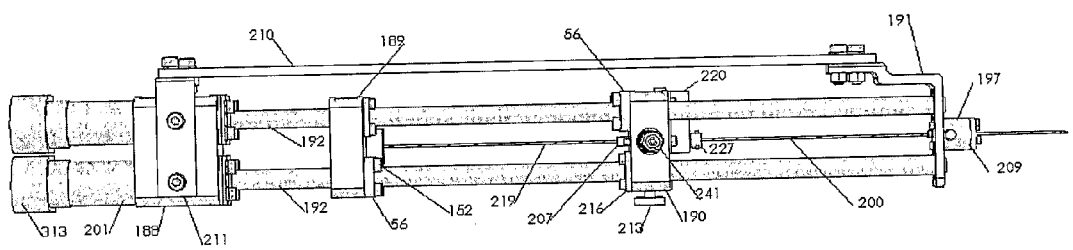
FIG. 6 and FIG. 7 are a top view and a front view of the 3D assembly of the needling mechanism.
Figure 7:
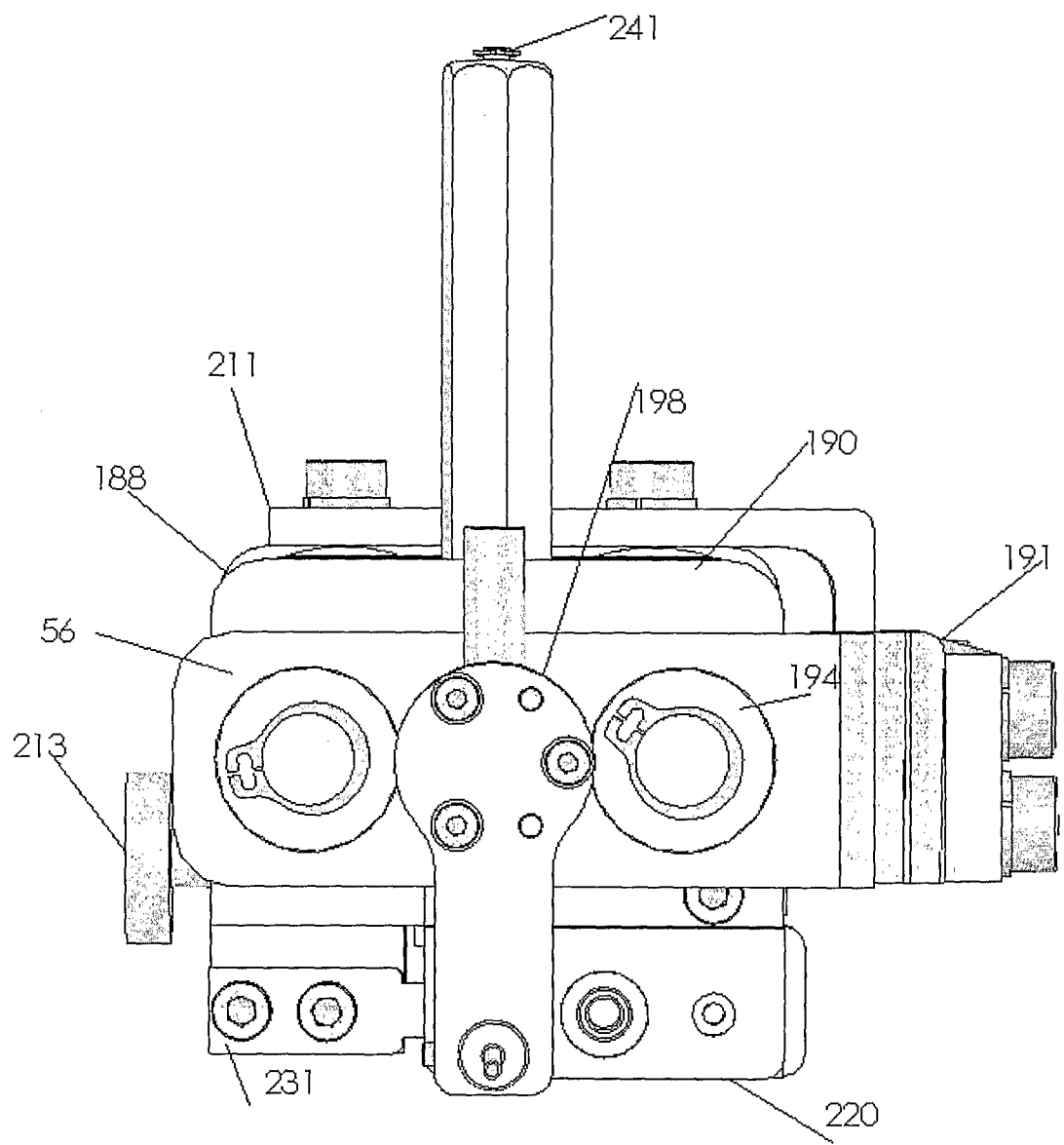

FIG. 5 to FIG. 7 show the perspective view, top view and front view of 3D assembly of the needling mechanism, in which plurality of radioactive seeds are delivered into the patient's body for tumor treatment, for instance, prostate cancer low dose brachytherapy. In FIG. 5, most of the key components are shown including encoders 313, motors 201, ball screws 192, moving stages 189/190, stylet 219 and cannula 200, cannula rotation transmission gears 224/226, seed cartridge 241, etc.

The key parts of the device are the cannula 200 which is a hollow needle allowing radioactive seeds passing through into the required locations of the patient's body, a stylet 219 taking the task of pushing the seeds, and two moving stages driving cannula 200 and stylet 219 by the ball screw transmission driven by two motors 201.

To improve the friction status of cannula 200 with tissue while inserting, the cannula 200 is driven to rotate in some speed, this rotation is transmitted by three small spur gears 224/226. The rotation motion greatly reduces the friction force of insertion and increases the targeting accuracy of cannula 200 tip and also the seed implantation location. A commercial seed cartridge 241 is arranged in the top position of the device and held by the cartridge holder 207 which is positioned by a spring plunger 212 and can be easily tightened by a knob 213.

The cannula 200, stylet 219 and all the sterilizers can be easily loading and unloading by the special design structures.

There are a total of three force sensors included in this device, two z-direction force sensors 233 installed in the back end of stylet 219 and cannula 200 for detecting insertion force, one x-y force sensor 197 installed in the front supporting point detecting cannula transverse forces and torques. Optical encoders 313 are also included which are installed in the back end of the motors 201. These sensors ensure the emergency case detection and the application of a closed-loop automatic control system.

Figure 8:
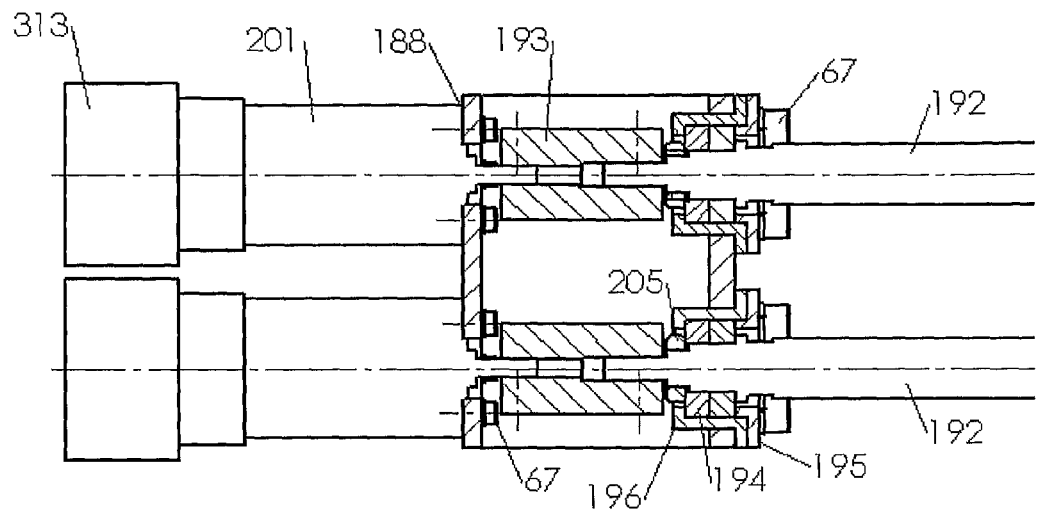
FIG. 8 is a sectional view of the portion of the motors of the needling mechanism, couplings, encoders, bearings and ball screws. The transmission relation in this area is shown in detail.

In FIG. 8, the connection structure among the motors 201, couplings 193, bearings 196 and ball screws 192 is shown in the pattern of 2D section view of the needling mechanism. Optical encoders 313 are attached to the back side of the motors 201 for rotation angle detection. Motors 201 and ball screw shafts 192 are directly connected by couplings 193. The ball screw shafts 192 are fixed purely by the shaft thrust nuts 205 and the two bearing sets 196. All the components in this portion are supported by the bracket part 188 which is connected to the side board 210 with an angle connection board 211.

Figure 9:
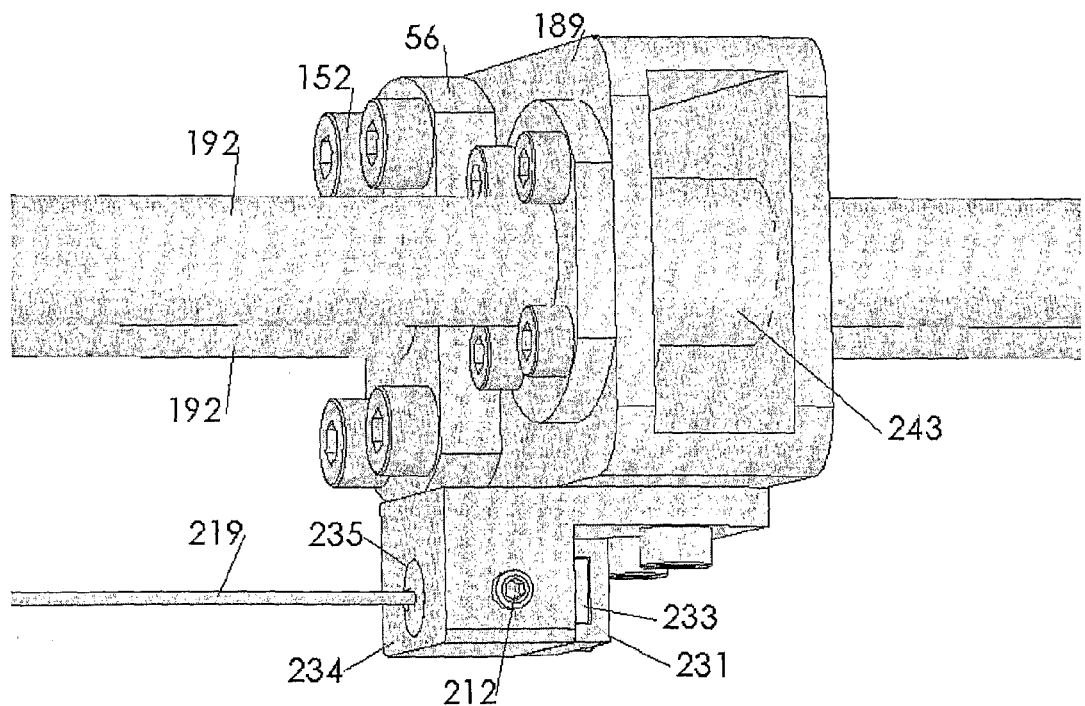
FIG. 9 shows the 3D view of stylet moving stage including stylet force sensor holder, stylet z-direction sensor, stylet sterilizer, plunger, etc.
Figure 10:
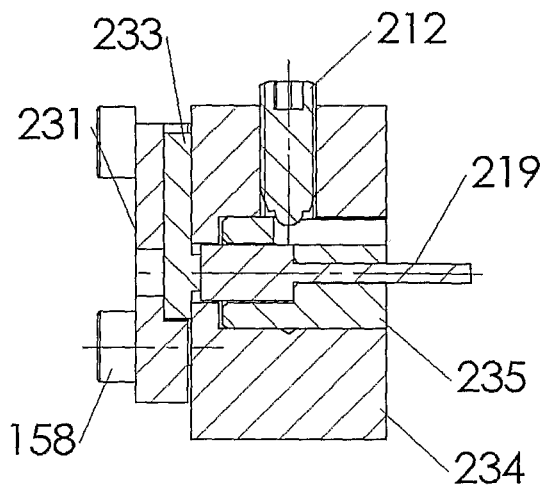
FIG. 10 shows the 2D structure of stylet holder, sterilizer, plunger, force sensor and sensor holder in detail.
Figure 11:
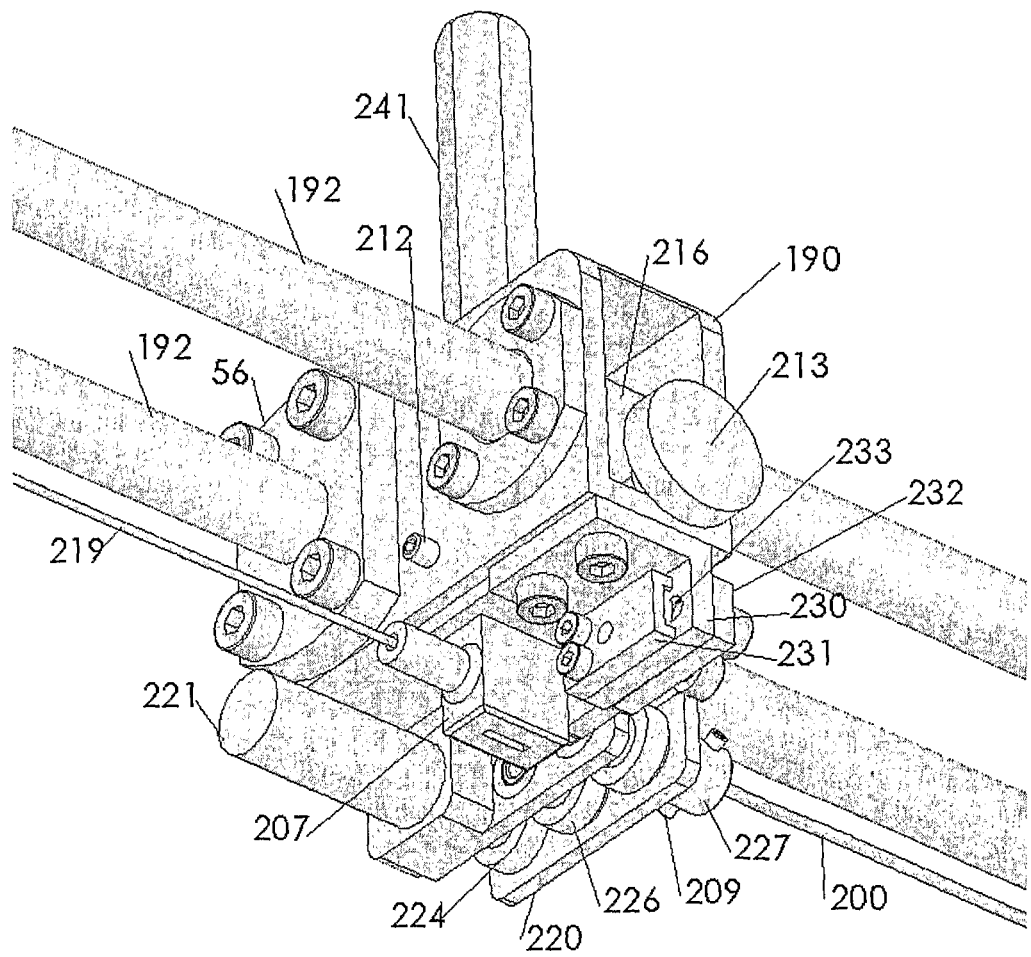
FIG. 11 shows 3D view of cannula moving stage including cannula force sensor, seed cartridge holder, cannula rotation drive motor and spur gear transmission, the commercial cartridge, etc.

Stylet moving stage which is shown in FIG. 9 comprises a support box 189 holding ball screw nut 56 and bushing 243, stylet holder 234 (shown in FIG. 10) together with stylet sterilizer 235 and a z-direction force sensor 233 and its mounting block 231, and a plunger 212.

While the ball screw shaft 192 in the left side is driven to rotate, the box 189 will be driven to move along axial direction, the whole stylet moving stage moves with the box 189. Although the right side ball screw shaft 192 does not drive the box 189, it supports the box 2 by the bushing 243.

The stylet sterilizer 235 is necessary for sterilization need in surgery operation, this part will be installed together with the stylet needle 219 just before the seed delivery procedure. The stylet sterilizer 235 has counterbore holes along its center line which just hold the stylet head inside and allow it rotate and move backward to be against the force sensor 233 top surface for the axial force detection of the stylet 219. There is a long groove in the outside surface of the sterilizer 235, to allow the spring plunger 212 to tighten it and hold it in position, by which the stylet 219 can also be taken out while big enough force is applied. This structure ensures the stylet 219 to be easily loaded and unloaded. A force sensor holding block 231 which can be installed from back side by screws 196 is used to fix the sensor 233 and arrange the sensor's wire along its opening side wards. The stylet center line is just located in the middle plane between the two ball screws shafts 192.

Figure 12:
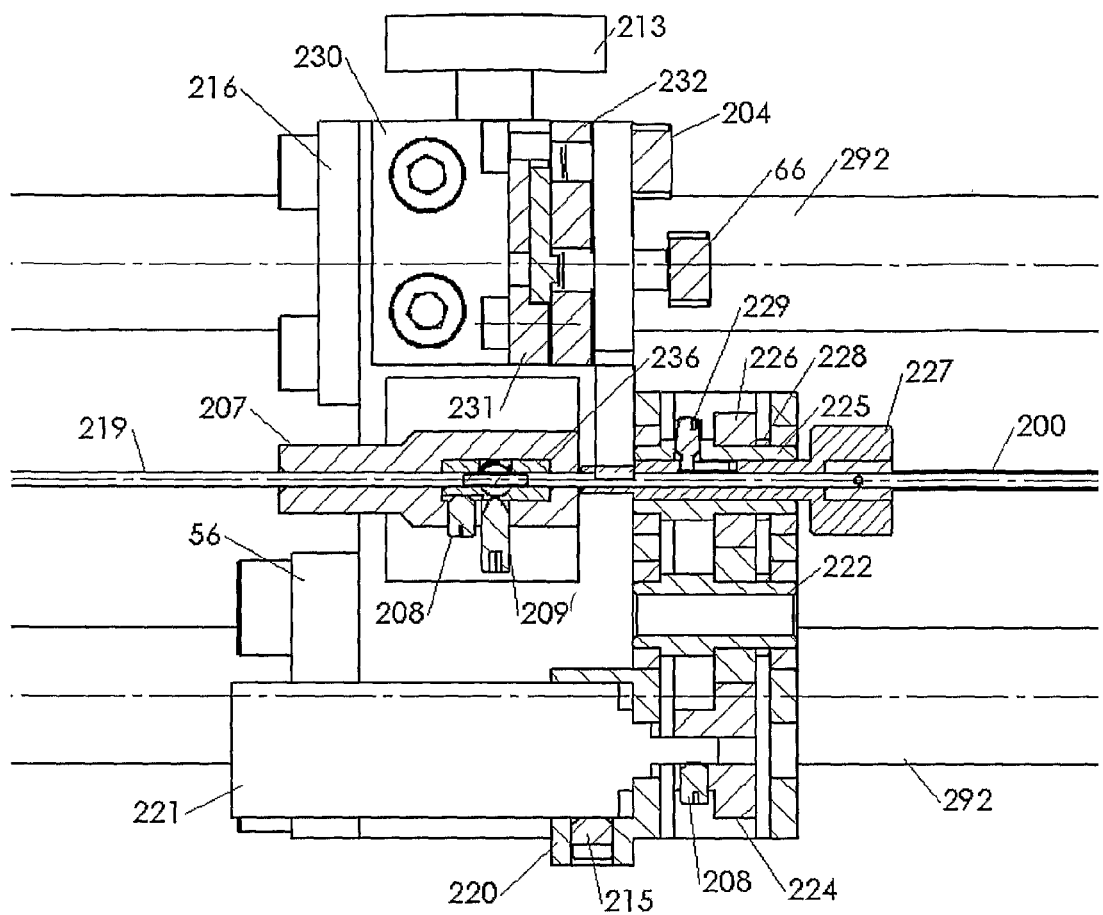
FIG. 12 shows the section view of cannula moving stage and cannula rotation drive, cannula force sensor, seed cartridge holder, ball screws, etc, in detail.
Figure 13:
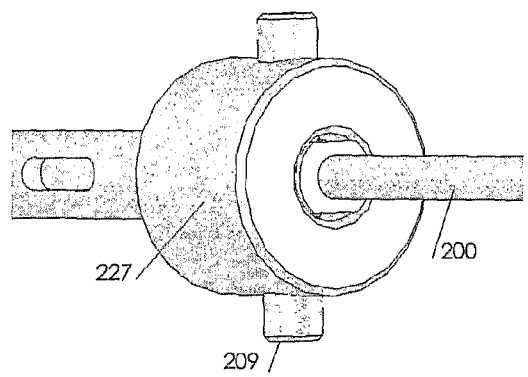
FIG. 13 is the 3D view of cannula sterilizer which is also used as cannula holder.
Figure 14:
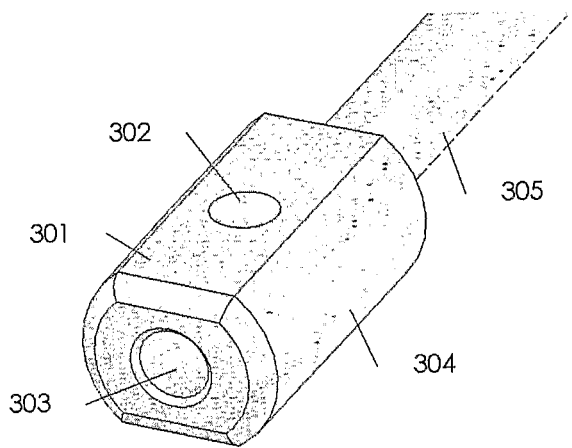
FIG. 14 is the 3D structure of the special designed cannula head for easy loading and unloading with cannula sterilizer.

The moving cannula stage and other attached structures are shown in FIG. 1 (3D view) and FIG. 12 (section view) and also by FIG. 13 and FIG. 14.

The main support part of the cannula moving stage is the support box 190 in which a ball screw nut 56 and a bushing 216 are held by two holes allowing the two ball screw shafts 192 passing through. In FIG. 7, the right ball screw shaft 192 which drives the nut 56 in stylet moving stage supports the box 190 and forms a slide bearing together with the bushing 216.

The seed cartridge holder 207 is mounted in the bottom surface in the middle position where there is a hole to allow the seed cartridge 241 to pass through into its holding position in the holder 207. Because the cartridge holder 207 will be passed through by the radioactive seeds, cannula 200 and stylet 219 which will be pushed and inserted into the patient's body, the sterilization is needed before use. So, easy loading and unloading function is necessary for the cartridge holder 207. An outstretched round column portion in the cartridge fits with the hole in the bottom surface by which the cartridge holder is restrained purely together with a positioning plunger 212. The cartridge holder 207 is tightened by the tightening knob 213 which is located in side place of the support box 190 and is operated by operator's hand manually. The commercial cartridge 241 is arranged in the top of the support box 190 and is installed into the holder with its body passing through the box 190. Two spring plungers 208/209 position and tighten the cartridge respectively, keeping it in its position while seed implanting.

The cannula 200 rotation is driven by a small DC motor 221 through spur gear 224/226 transmission, which is supported by a gearing bracket 220 mounted to the support box 190. A total of three small spur gears including an idle gear 226 are included for a little far distance transmission between the motor shaft 221 and the cannula shaft 200.

The cannula sterilizer 227 is used also as the cannula holder holding the cannula's back head with two spring plungers 209 which are arranged by 180 degree. Two flat planes 301 with a small hole 302 each are cut in the cannula head 304, in which the front balls of the plungers 209 fit with the two holes 302 to ensure the good positioning and tightening of the cannula 200 inside the sterilizer 227.

The cannula sterilizer 227 is used also as the axial force transducer from the cannula 200 to the force sensor link 232. Its movement is restrained by the plunger 229 along its axial direction, in which it can only push the sensor link 232 backward, the reverse side movement is blocked. The plunger 229 also mounts the sterilizer to the spur gear shaft 225 together with the gear 226, so that the cannula 200 can be driven to rotate while needed. The sterilizer 227 pushes the sensor link 232 by its shoulder, and is connected to the sensor base 230 by screw 204 which is also the rotation joint of the link. The force will be acted on the force sensor's acting point by another screw 66 which is threaded together with the link 232. The force sensor 233 is arranged in the back side of sensor base 230 and is fixed by the sensor block 231.

Figure 15:
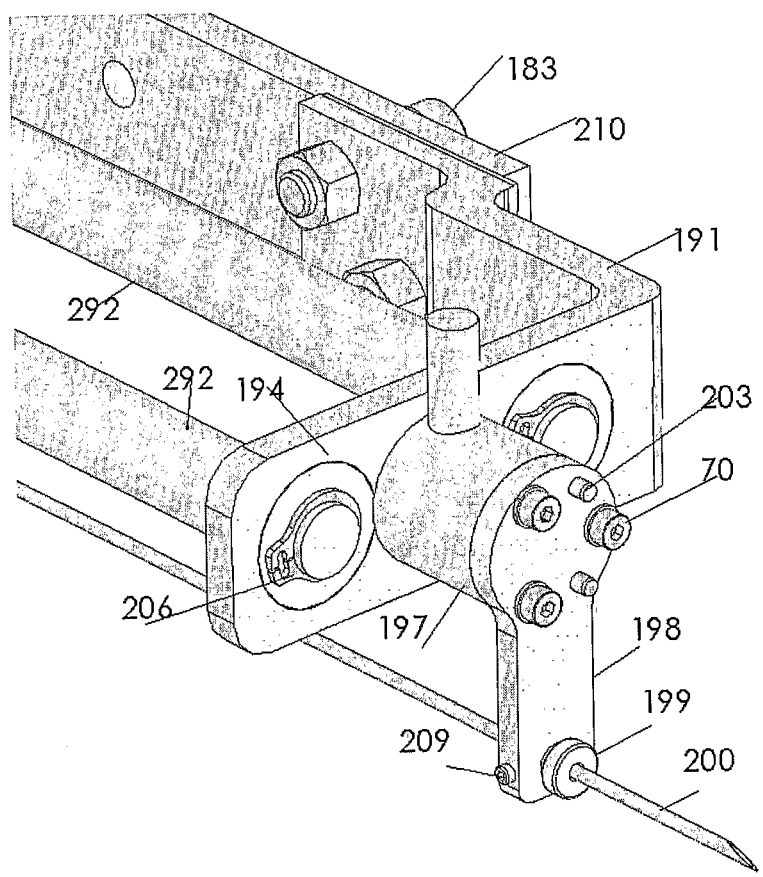
FIG. 15 shows 3D view of the front portion of the device, including front support board, bearings, x-y force sensor, sterilizer, cannula.
Figure 16:
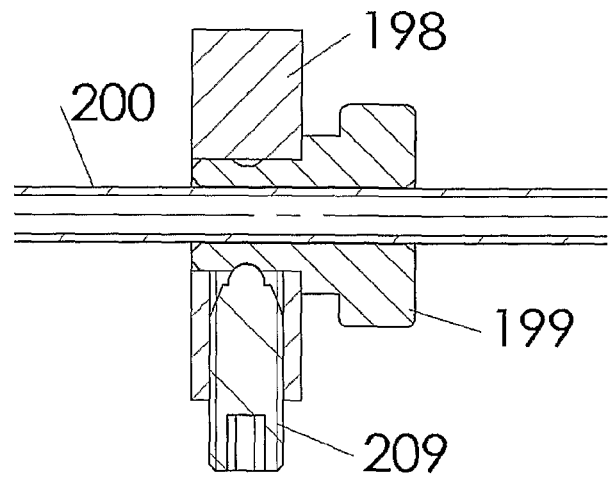
FIG. 16 is section view of structure and connection relation of the cannula sterilizer, the plunger, the front support and the cannula.

FIG. 15 and FIG. 16 show the front end structure of the needling mechanism. Two ball screw shafts 192 are supported by the front block 191 with two bearings 7 which are restrained by retaining rings 206. The front board 191 is made to "S" shape in its connection point with side board 210, for reducing the front end width of the whole device which is a very important character considering the narrow width in the patient body's treatment area. The x-y force sensor 197 is used for detecting the transverse forces and torques of the cannula 200 while inserting, which is also the base of the front support 198 supporting the cannula 200 at the location close to the patient's body. The front support 198 is positioned to the x-y force sensor 197 by two positioning pins 203, and mounted by three screws 70. The sterilizer 199 is made to the easy operated shape and is necessary to insulate the cannula 200 and the front support 198 which maybe contaminated. A plunger is used to fix the sterilizer 199 by fitting its front ball into the round groove. This is also an easy loading and unloading design.

Figure 17:
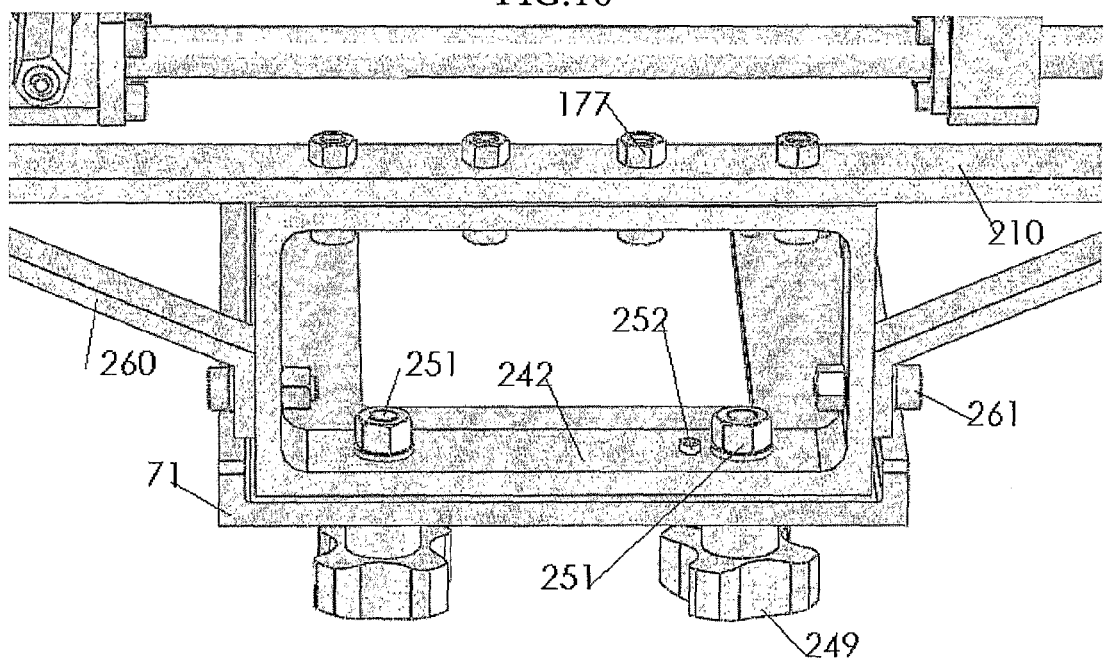
FIG. 17 is a perspective view of the angulations structure.
Figure 18:
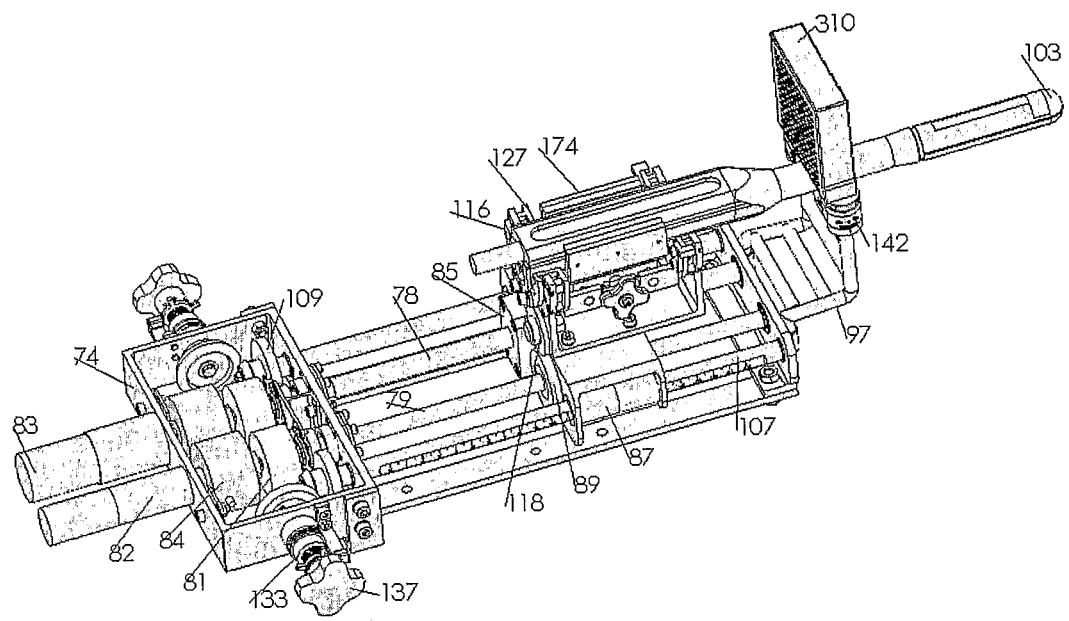
FIG. 18 is a perspective view of the ultrasound probe driver for prostate imaging or brachytherapy guiding. All the main parts of this mechanism are shown, for example, motors, encoders, clutches, ball screw and ball spline, the half-ring bearing and clamp, the moving stage, the front frame and the stabilization needle guidance, etc.
Figure 19:
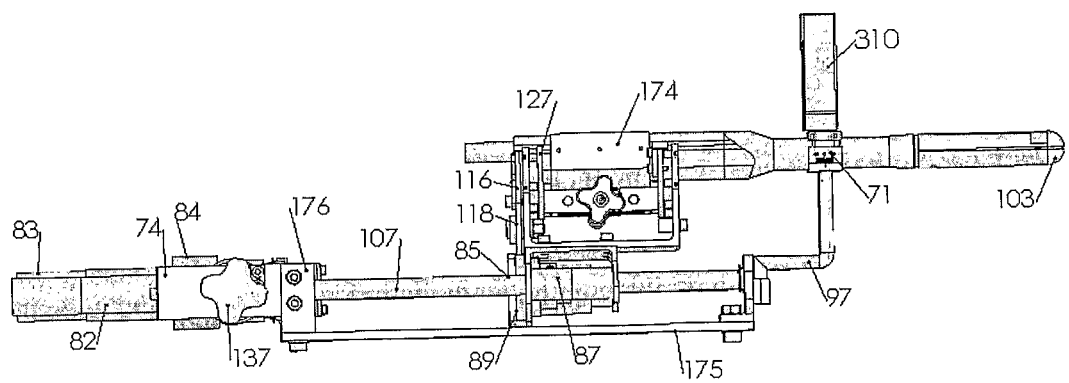
FIG. 19, FIG. 20 and FIG. 21 are a side view, top view and back view of the 3D assembly of this ultrasound probe driver.
Figure 20:
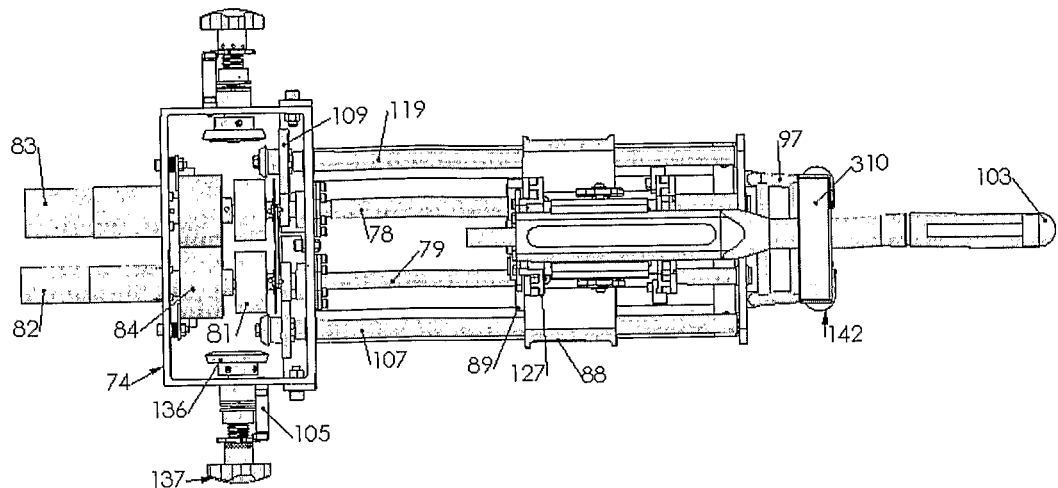
Figure 21:
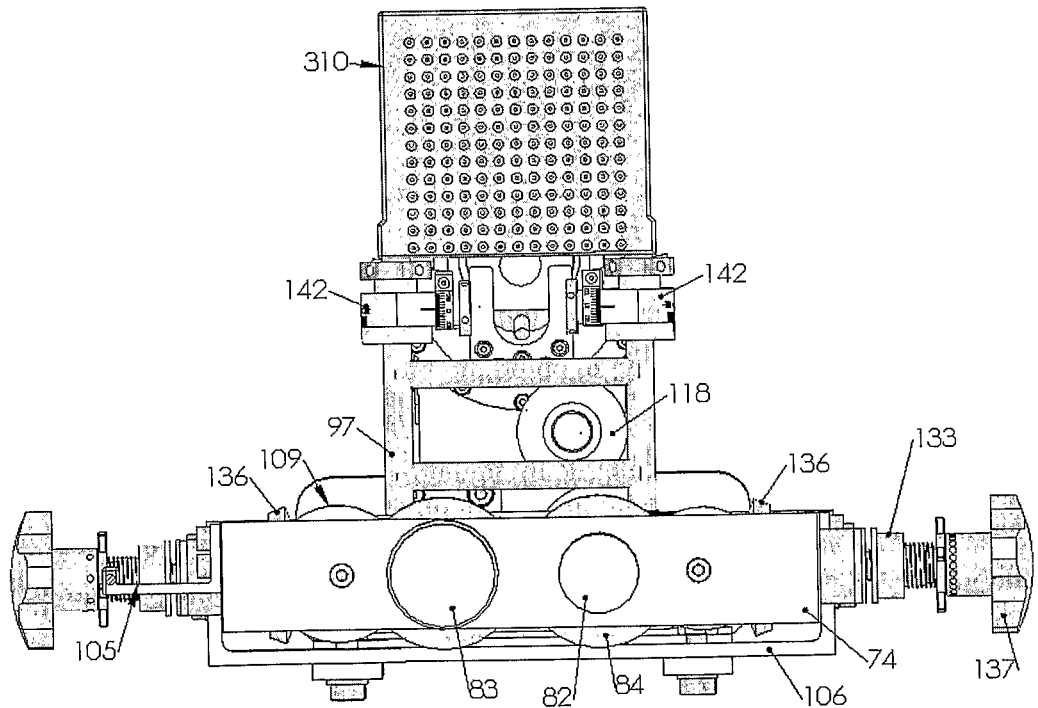

FIG. 17 shows the structure of the angulations and manual take over of the needling mechanism. Two shafts 251 are used to connect the 2DOF robot side board 71 and the support square component 242 of the needling mechanism. In the square component 242, the two holes are round and the shafts 251 are fixed there while working, and one hole is round and another hole is long flat to allow the shaft move around the other shaft in the side board 71, by which the angulations can be realized. The spring plunger 252 is used for positioning of the ±5° and parallel posture of the needling mechanism. The angulations adjustment should be done while the two knobs 249 are loose, and the manual take over happens while the two knobs 249 are taken out in which case the needling mechanism can be taken over to the side place to allow the manual operation possible.

FIG. 18 to FIG. 21 show the perspective view, side view, top view and back view of 3D assembly of the probe driver, in which an ultrasound probe 103 is included. The ultrasound probe 103 can achieve translational motion and rotation motion for longitudinal scanning and sagittal scanning respectively to the prostate or other internal organs. Motorized and manual driving modes can be chosen according to the operator's requirement or the working state of the mechanism. An optional front frame 24 in which a stabilization needle guidance 71 is installed can be used as the support of the template 25, which is a very important component in radiation brachytherapy treatment of prostate cancer.

Figure 22:
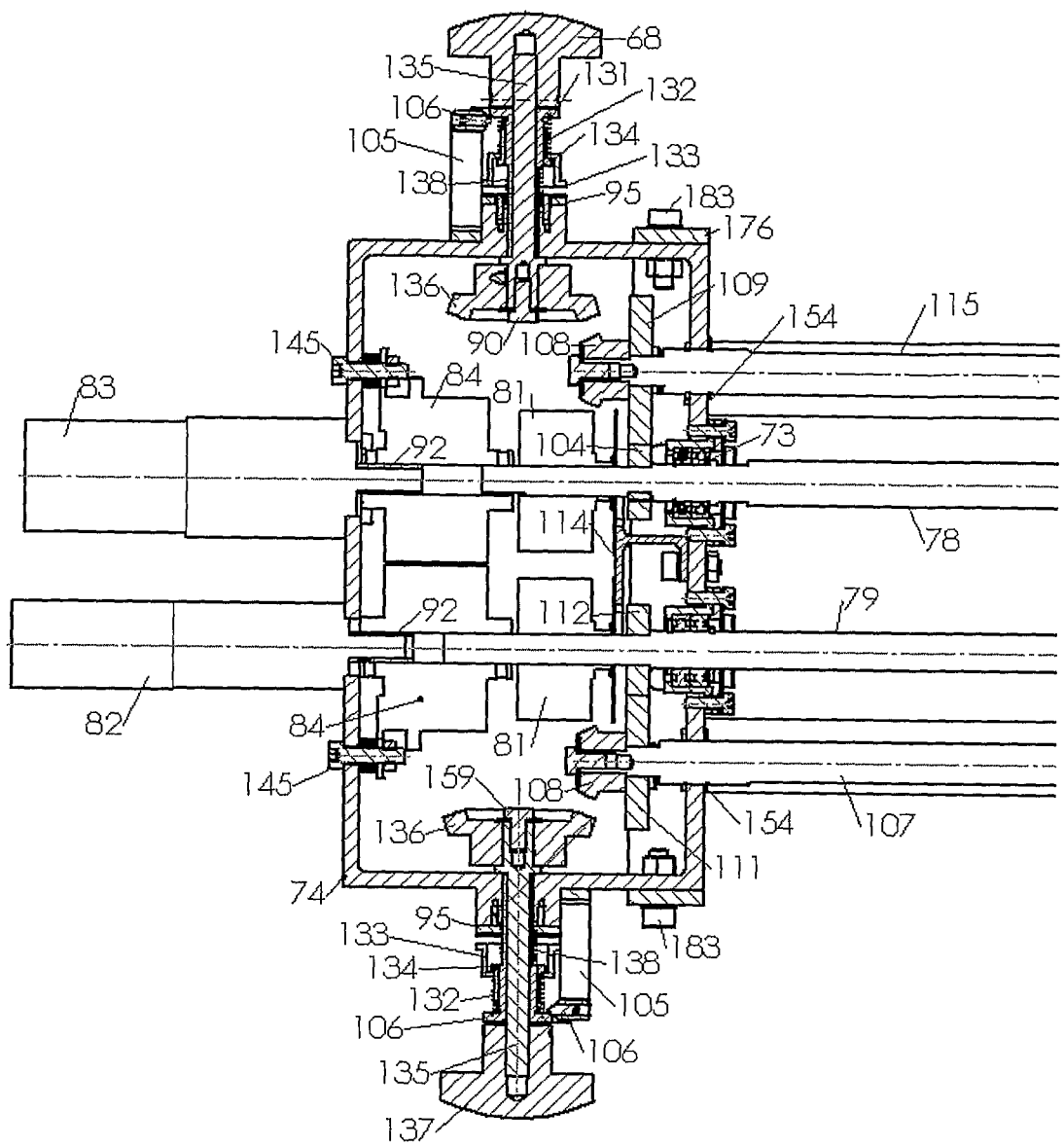
FIG. 22 is a sectional view of the portion of motors, clutches, encoders and hand knob transmissions in both sides of the probe driver.

FIG. 22 is a section view around the motors of the probe driver. Motors 82/83, clutches 84, drive knobs 137/139, bevel gears 136 and shaft bearings are all supported by a main square box 74. In the front end, a front end block 75 is arranged to support and fix the front frame 97 and the four shafts (ball screw 78, ball spline 79 and the two supporting rods 107/115). The whole mechanism is supported by two supporting boards 175 beneath the main square box 74 and the front end block 75. There are eight through holes arranged in the two supporting boards 175, by which the all mechanism can be mounted to the base or to other stable platform, and also can be mounted by other cooperation devices.

The transmission route of ultrasound probe 103's translation motion is from the translation motor 83 (a gear box is included for speed reduction and torque increasing), the electric clutch 84, encoder 81, ball screw 78, ball screw nut 85, the moving stage, the clamp and finally to the ultrasound probe 103. The ball screw 78 is used to obtain linear motion. The manual transmission route is from the left drive knob 139, to bevel gearing 136/108, to the united gears 109, then to the ball screw shaft 78, others are same with motorized route.

The transmission route of rotation motion is from the rotation motor 9 including a gear box, the electric clutch 84, encoder 81, ball spline 79, transmission spur gear 89, idle gear 118, half-ring gear 116, finally to the probe 103. The ball spline 79 is used to transmit rotation motion to another place accurately. The manual transmission route is from the right drive knob 137, to bevel gearing 136/108, to the united gears 111, then to the ball spline shaft 79, others are same with motorized route.

Figure 23:
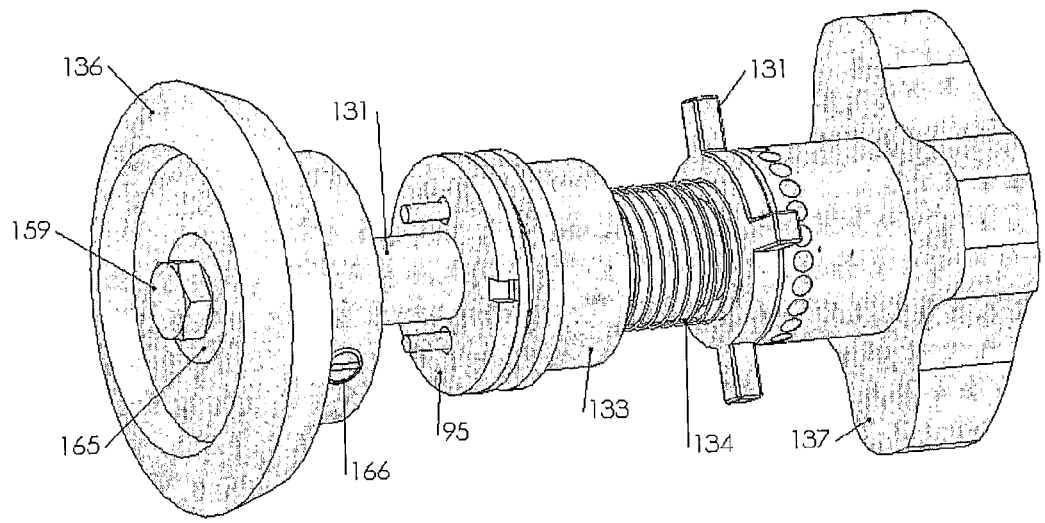
FIG. 23 shows the 3D view of the hand knob driving transmission to the ball screw and ball spine, and the electric switch controlling the motors connected or disconnected.

The switching between motorized and manual modes is controlled by the electric switches 95 which are installed inside the drive knobs mechanism shown by FIG. 23. When the operator pushes down the drive knobs 137/139 into their "engaging" positions, and turn the hollow shafts 131 which have four lateral detents in the top end to ensure one detent is hitched by the hooks 105, the bevel gears are engaged together and the turning motion can be transmitted from the drive knob 137/139 to the bevel gear 136 through the inner shaft 135 inside the hollow shaft 131. After that, the hollow shaft 131 will stay there without moving in the whole manual operation mode. At the same time, the electric switches 95 are connected as the control signal to make the electric clutches 84 released. This function guarantee the conflict won't happen between motorized and manual working modes. Two compression springs are used in the drive knob mechanism, one 138 is used to make sure the knob 137/139 and the bevel gear 136 can stay at its "release" position when the working mode is "motorized", the whole set will be pushed out from the main square box 74. Another spring 132 is used to guarantee the two poles of the electric switch 133 are touched together all the time, even when the knob 137/139 is turning.

United gears 109/111 which include one small bevel gear and one big spur gear are supported by the supporting rod 115, it can rotate freely around the supporting rod 115 by which the motion transmitted to the spur gear 104 fixed on the ball screw shaft 78.

Because the electric clutches 84 are made in English dimension system, the two connection holes in two sides are in $5/16"$, the motor output shafts are in metric system, 6 mm and in diameter, an adaptor component 92 is necessary.

The two encoders 81 are supported and connected directly to the ball screw shaft 78 and ball spline shaft 79. Set screws are used to fix the encoders' rotors with the shafts 78/79. An encoder bracket 114 is specifically designed to fix the outside part of the encoders to ensure no turn occur when the ball screw shaft 78 and ball spline shaft 79 turn.

Figure 24:
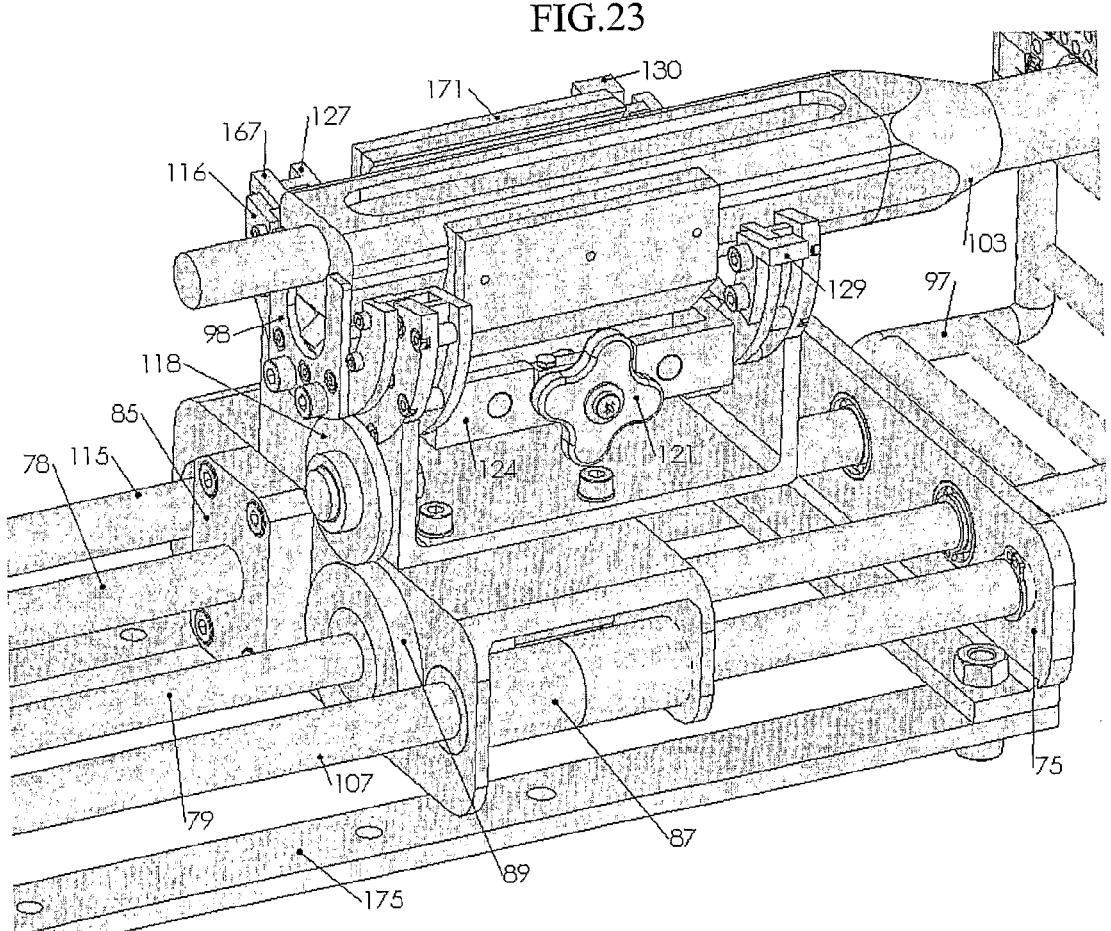
FIG. 24 shows the portion of the moving stage, the half-bearing and its spur gear transmission, and the tightening clamp.

FIG. 24 shows the moving stage, half-ring bearing and clamp assembly of the probe driver. The main skeleton of moving stage is a U-shape component in which there are four through holes mounting the ball screw nut 85, ball spline nut and the two bushings 87 for supporting guide rods 107. Ball screw 78 and ball spline 79 are arranged between the two supporting rods 107 for the best force balance.

Figure 25:
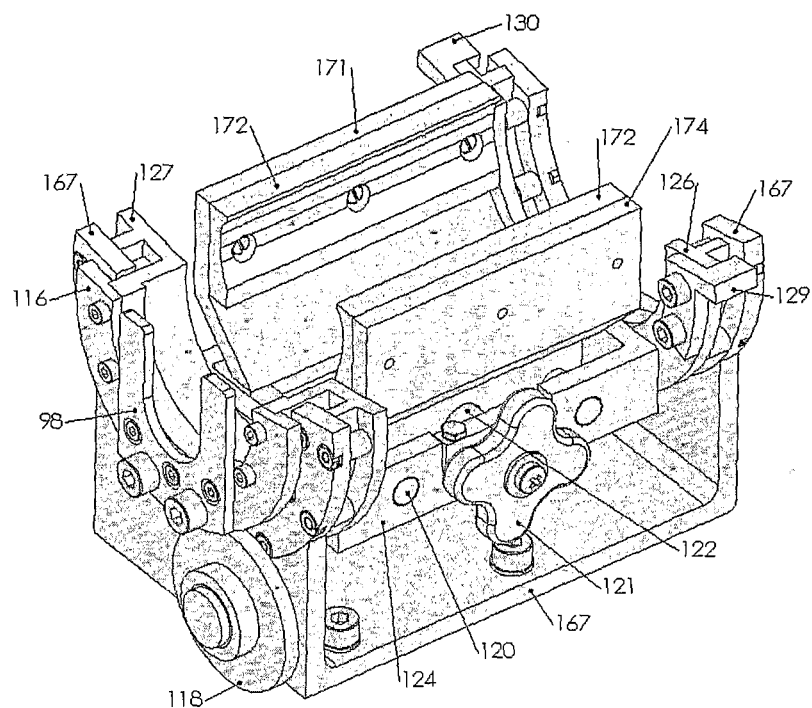
FIG. 25 shows 3D view of the half-ring bearing, the probe tightening clamp and other structure in this area.
Figure 26:
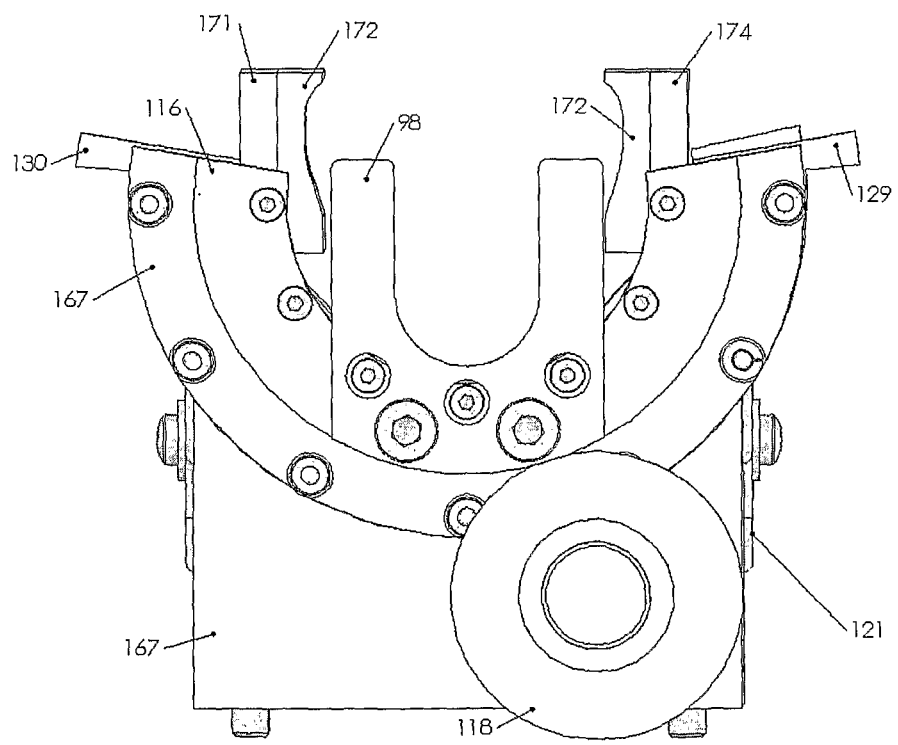
FIG. 26, FIG. 27 and FIG. 28 shows the back view, side view, and explode view of the structure of the portion of half-ring bearing and probe tightening clamp.
Figure 27:
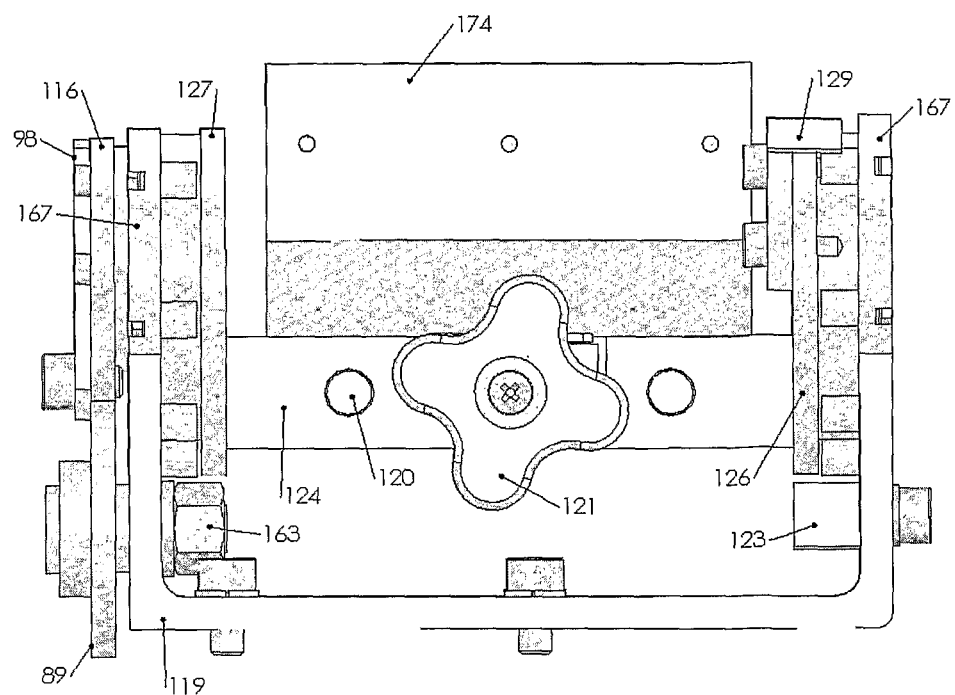
Figure 28:
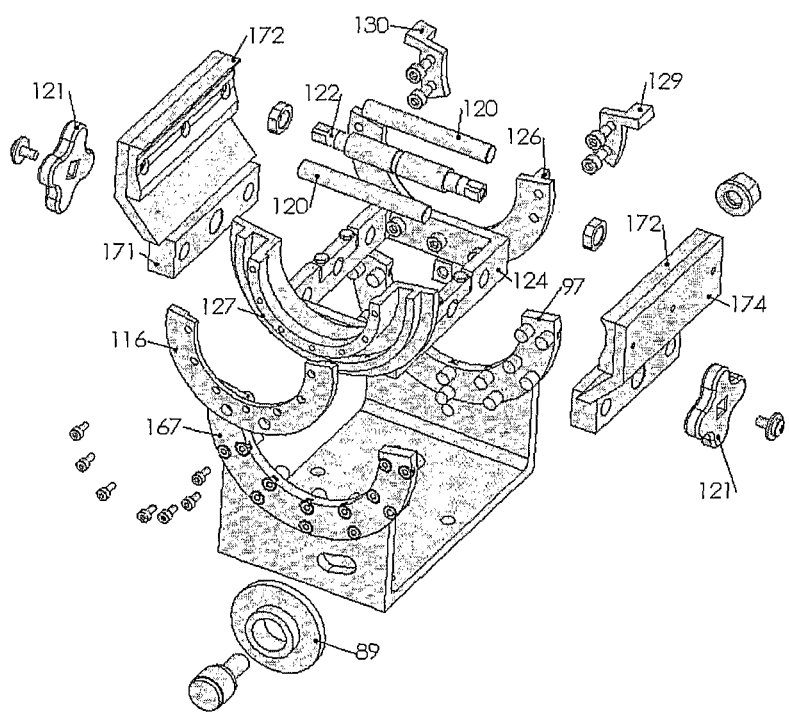

On the moving stage is the half-ring and clamp assembly show by FIG. 25 which is mounted by four screws together. FIG. 26 and FIG. 27 are the back view and side view of the half-ring bearing and clamp assembly without the ultrasound probe 103, FIG. 28 is its explode view. Bearing base 167 is the supporting part of half-ring bearing and clamp assembly in which both of static part of half-ring bearing 167 are mounted and fixed in two sides. In each static part of half-ring bearing 167, fourteen cam followers are arranged to two circular half ring 167 with some accurate distance in which the rotation part of half-ring bearing 127 rotate around. The cam followers support and restraint the rotation part 127 to obtain its rotation motion in some degree. The half gear 116 which is driven by the idle gear 118 is connected and fixed to rotation part of half-ring bearing 126/127. The idle gear 118 is driven by the transmission spur gear 89 connected together with ball spline nut. The clamp frame 124 is mounted between and with two side's rotation part of half-ring bearing 126/127. The up-down and left-right positions of the clamp frame 124 are calculated carefully to ensure that the probe 103's center line just coincident with the rotation center of the half-ring bearing.

Positioning piece 98 is used specifically for the axial positioning of the probe, by touching of the side surface of positioning piece 98 with the rear end surface of the ultrasound probe 103.

Inside the clamp frame 167 are reverse directional thread shaft 122 and two guide shafts 120. Two clamp jaws 171/174 are restrained by the two guide shafts 120 and move along their axial direction. There are reverse directional threads in left and right portions of the drive shaft 122 which is driven by the two tightening knobs 121. This structure feature of the drive shaft 122 guarantee that the two clamp jaws 171/174 can move closely(tightening) or fatherly(releasing) with only one turn to the tightening knobs 121. Two tightening knobs 121 are installed in both ends of the drive shaft 122 for the easy access and convenient operation. Another advantage of this design is that the clamping has the feature of self-locking which guarantee the probe 103 stabile enough when it is being held.

A rubber clamp pad 172 is used in each clamp jaw 171/174 aiming to obtain bigger gripping friction force.

Static dead block 123 and rotational dead block 129/130 are used to restrain the rotation part of half-ring bearing 126/127 inside the static part of half-ring bearing 167, and also to obtain the home position of rotation motion. Two rotational dead blocks 129/130 are arranged at both ends of the rotation part of half-ring bearing 126, the static dead block 123 is arranged at the side wall of clamp frame 119. For the embodiment shown in FIG. 8, the rotation angles in both directions are 90.5 degree.

The idle gear 89 mounted on clamp frame 119 by a bigger cam follower 163 which can move along a circular groove to adjust engaging status of the gearing.

Figure 29:
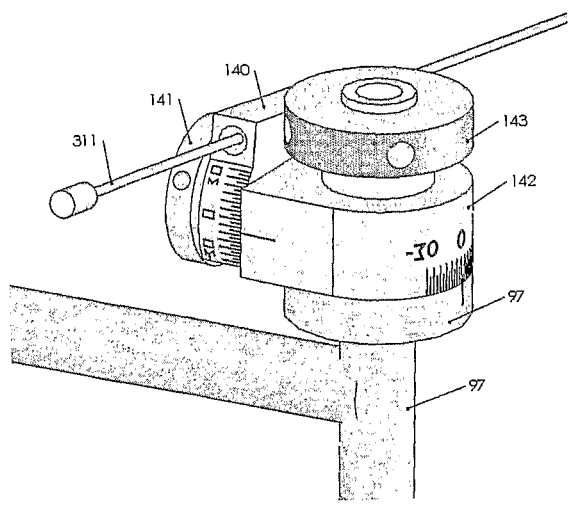
FIG. 29 shows the stabilizing needle guidance structure in 3D view which is supported by the front frame.
Figure 30:
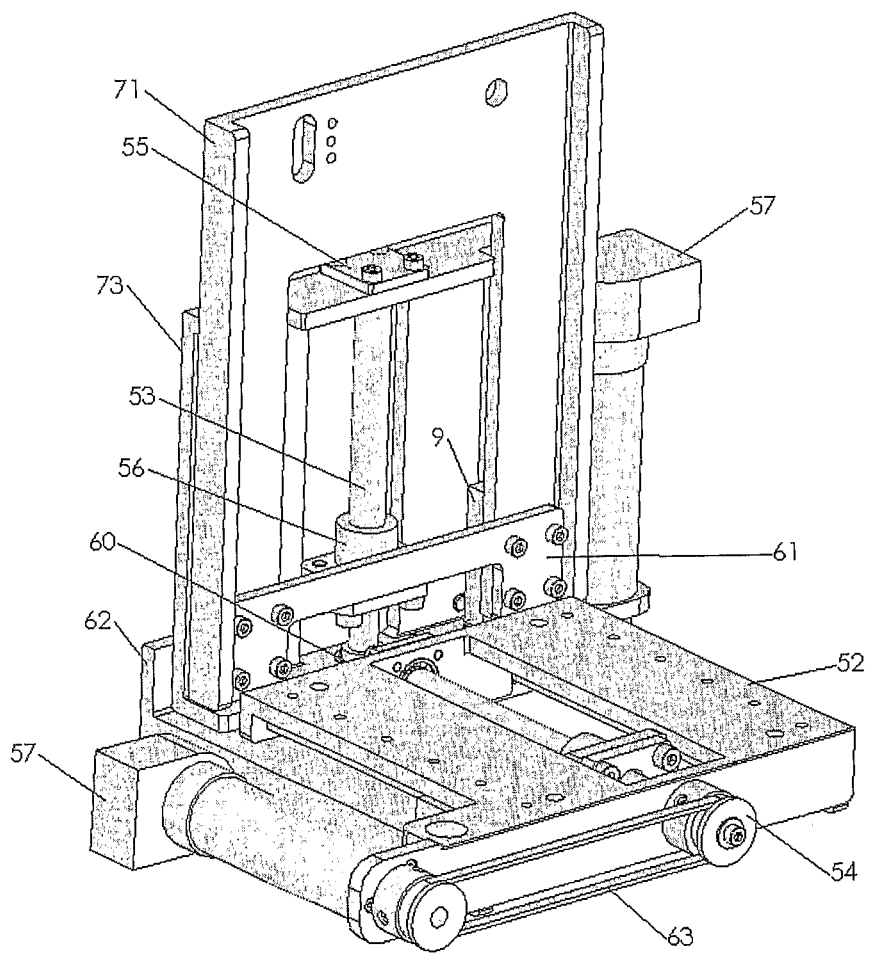
FIG. 30 is a perspective view of the 2DOF robot. All the main components are shown, including the two motors and encoders, guide rails and carriers, ball screws, timing belts and pulleys, etc.
Figure 31:
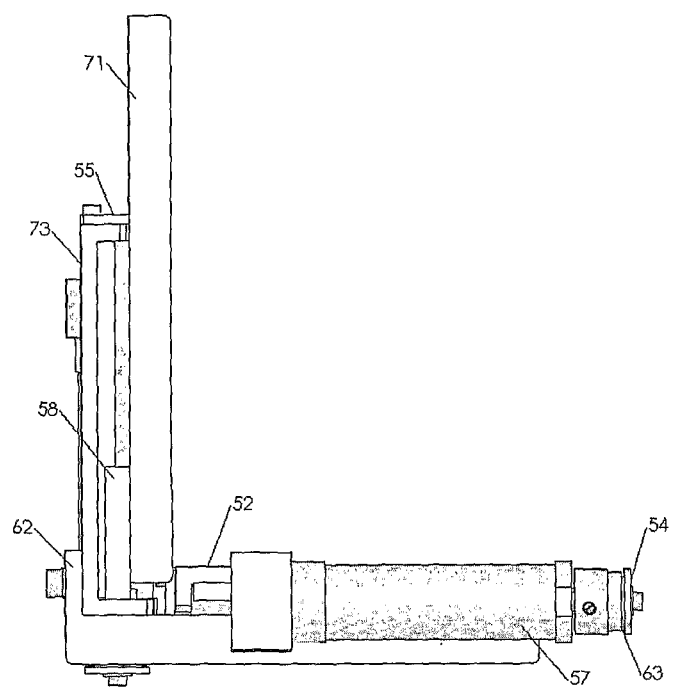
FIG. 31, FIG. 32 and FIG. 33 are the back view, top view and bottom view of the 2DOF robot.
Figure 32:
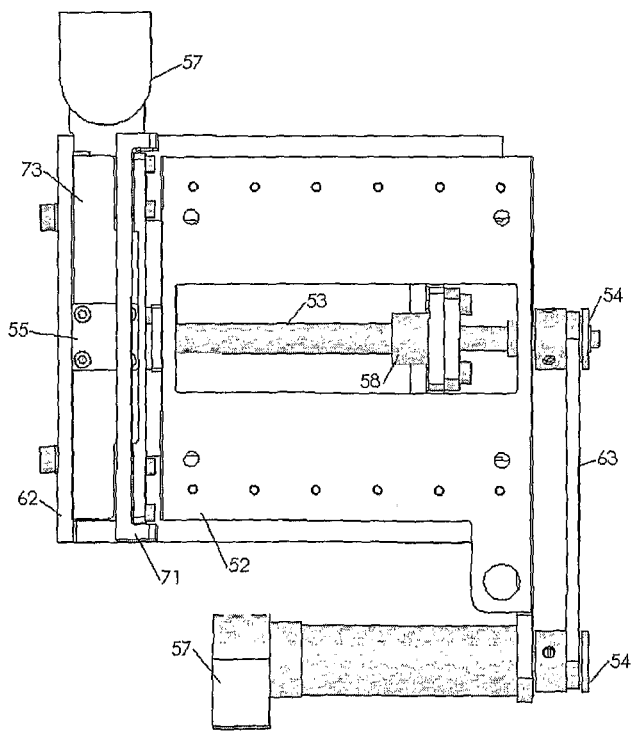
Figure 33:
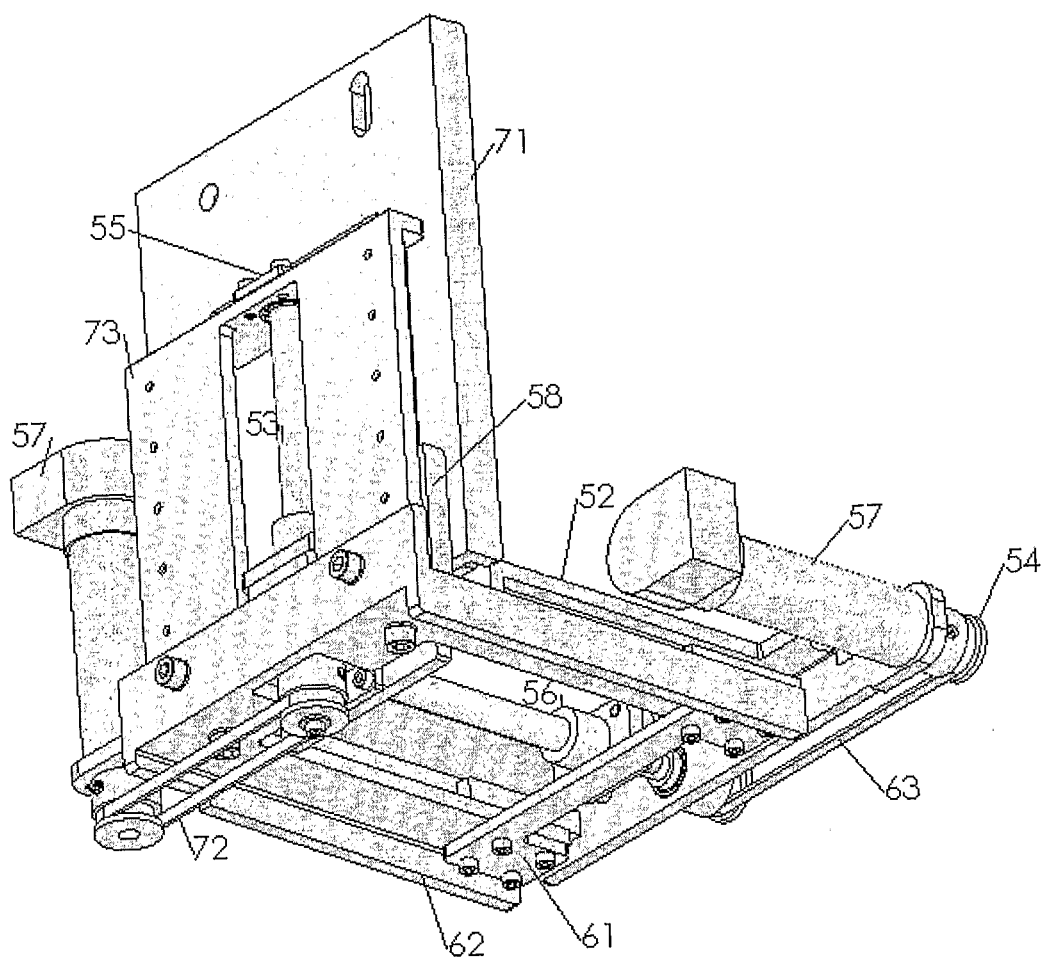

FIG. 29 shows one of the two stabilization needle guidance structure by which two stabilization needles 311 are guided in left and right sides just below the template 310 and supported by the front frame 97 which is an optional component, used in the case of low dose radiation brachytherapy to prostate cancer. The guidance mechanism has two degree of freedom which are rotations about X axis and Y axis. The angles about X and Y axes are displayed by the scales and numbers carved in its side. This part can be tightened onto front frame 97 by Y tightening nut 142. The same case to X adjustment part 140 and its tightening nut 141. The guide hole is located at X adjustment part 69 and supported by Y adjustment part 142. So, the guide hole obtains two degree of freedom adjustments.

FIG. 30 to FIG. 33 show the 2DOF robot, by a perspective view, back view, top view and bottom view. Two DC motors with encoders 57 are used for driving the two ball screws 53 to obtain the x and y direction movement of the needling mechanism. Timing belt transmissions 63 are used between the motors 57 and the ball screw shafts 53 which have a little big distance. Guide rails and carriers 58 are used for support and guide of the two translation joints. This mechanism is just arranged below the ultrasound probe driver and in its side place for the most compact structure of the whole system.

Figure 34:
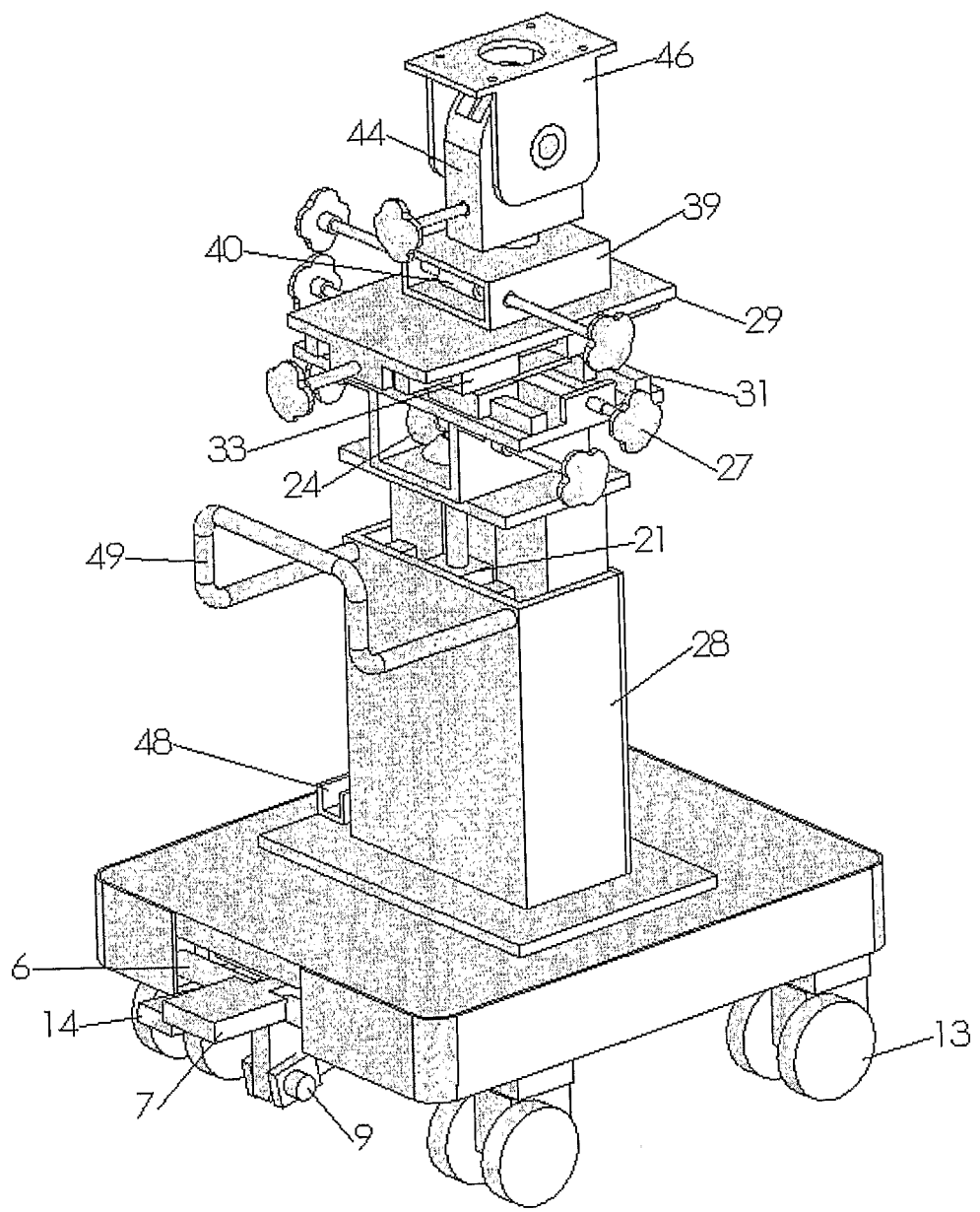
FIG. 34 shows a perspective view of the 5DOF passive platform and the cart.

FIG. 34 shows the perspective view of the 5DOF passive platform and the cart. The passive platform includes two revolute joins 46/39 with worm gear transmission, two horizontal translation joints 31/33, and one vertical translation joint with lead screw transmissions 28. A pair of bevel gears 24 is also utilized in the vertical translation joint for turning a 90 degree angle to allow easier access by hand to the knob. All the five joints are operated manually.

Figure 35:
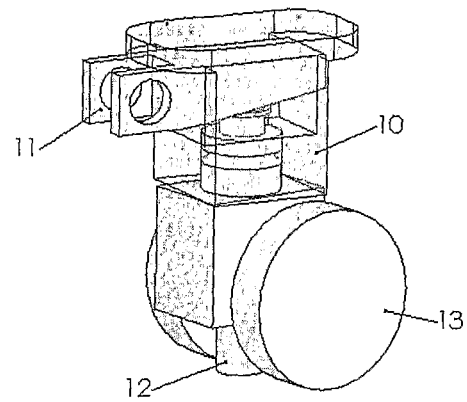
FIG. 35 shows a perspective view of the caster assembly with tightening wedge.
Figure 36:
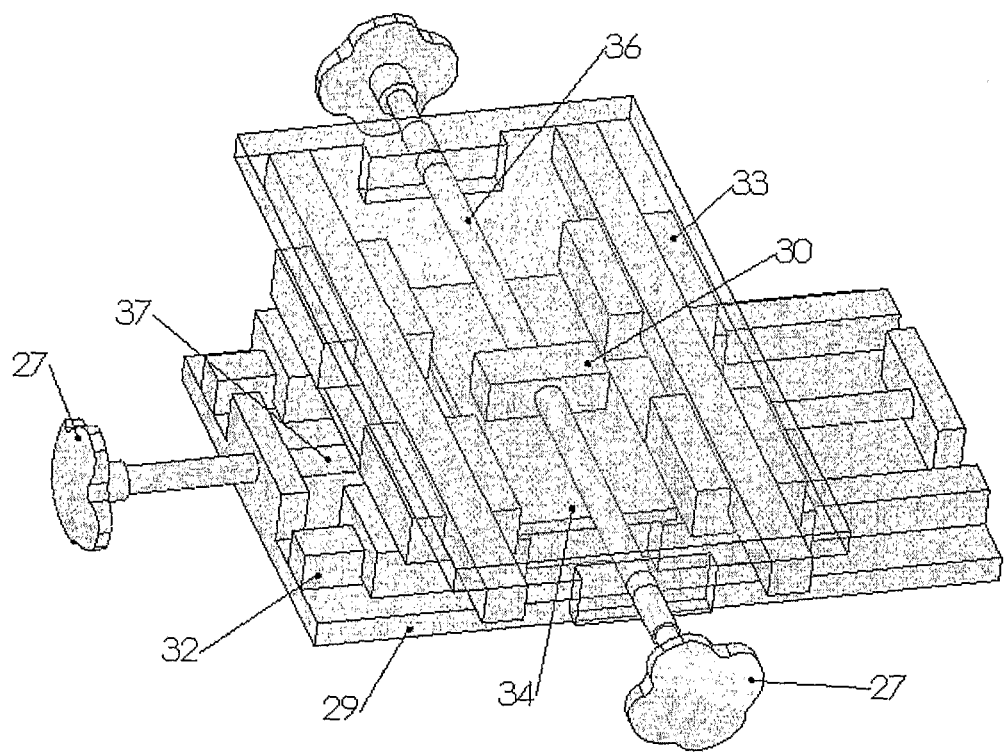
FIG. 36 is the structure of the two horizontal translation joints of the 5DOF passive platform.
Figure 37:
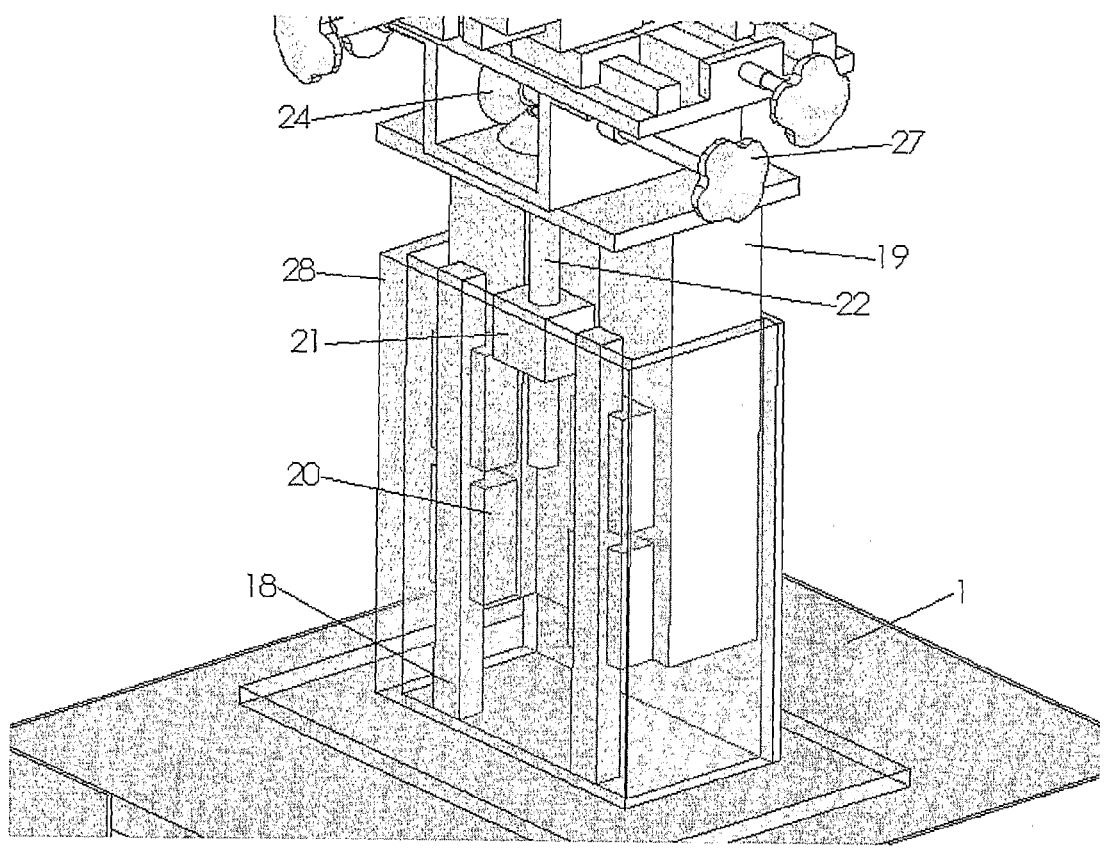
FIG. 37 is the structure of the vertical translation joint of the 5DOF passive platform

FIG. 35 shows a perspective view of the caster assembly with tightening wedge 11. A support foot 12 will stretch out to be against the ground to support the whole weight of the machine together with other same three feet. This support way is more stable than the way supporting by the wheels. FIG. 36 and FIG. 37 are the structures of the two horizontal translation joints and the vertical translation joint, in which lead screws 37/36/22, nuts 30/21, guide carriers 33/20 and guide rails 31/32/18 are shown.

Figure 38:
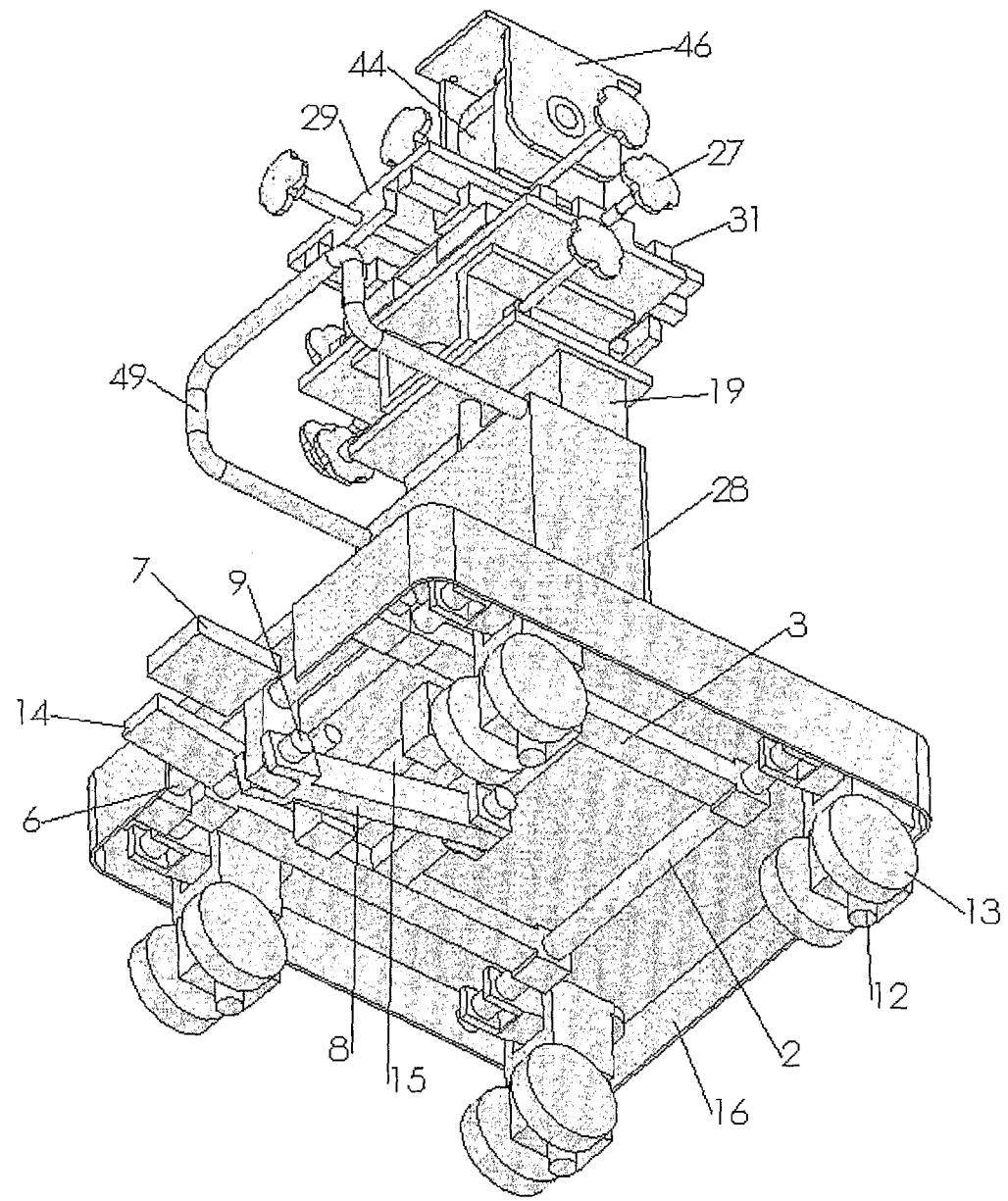
FIG. 38 shows the bottom view of the 5DOF passive platform, in which the detail structure of link mechanism of the cart is shown.

FIG. 38 shows the bottom view of the cart, in which the detail structure of link mechanism 8, the wedges 11, the wheels 13, the control pedals 7/14 are all shown. Two pedals 7/14 are designed used to activate the feet support function or release it.

Another aspect of the invention involves stabilization of the seeds in the prostate (or other organ). The system disclosed above can be equipped with various components for stabilization. One possibility is to coagulate the tissue between seeds, e.g., by diathermy or lasers. Coagulation by diathermy and by lasers is known in the art; however, its use in the context of the present invention is deemed to be novel. Another possibility is to dispense biological glue between the seeds while they are being deposited. Examples of biological glues which can be used are fibrin and BioGlue®, produced by Cryolife Inc. in Georgia.

A second preferred embodiment will be disclosed with reference to FIGS. 39-43. As noted above, the first and second preferred embodiments can be used together. They may also be used separately.

Figure 39:
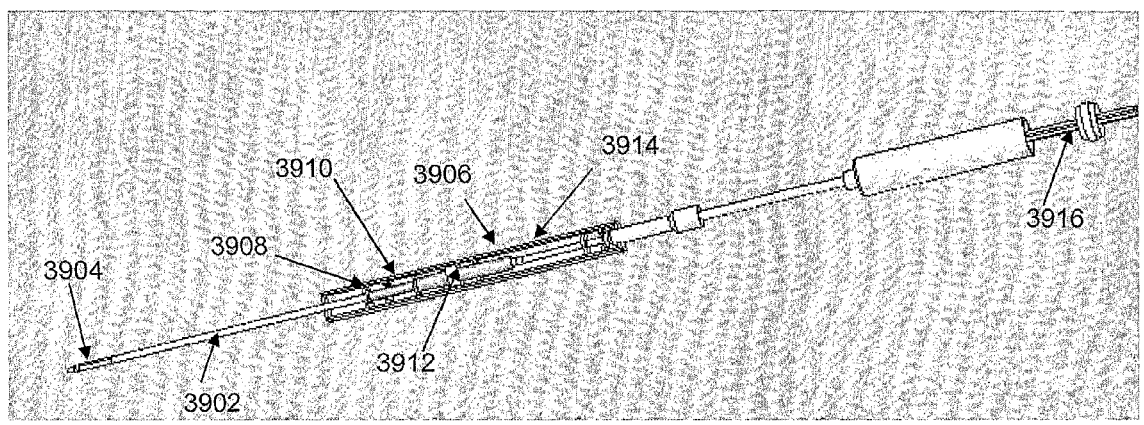
FIGS. 39-43 show the biopsy or brachytherapy needle insertion device according to the second preferred embodiment.

FIG. 39 shows a rotating needle assembly 3900 according to the second preferred embodiment. The assembly 3900 supports a needle 3902, which includes a stylet 3904. The assembly 3900 includes a case 3906 in which are disposed a cannula gear 3908, a cannula support 3910, a cannula screw 3912 and a stylet gear 3914. The assembly 3900 is connected to a tissue collecting syringe 3916 which is connected to a source of motive power for rotating the needle.

Figure 40:
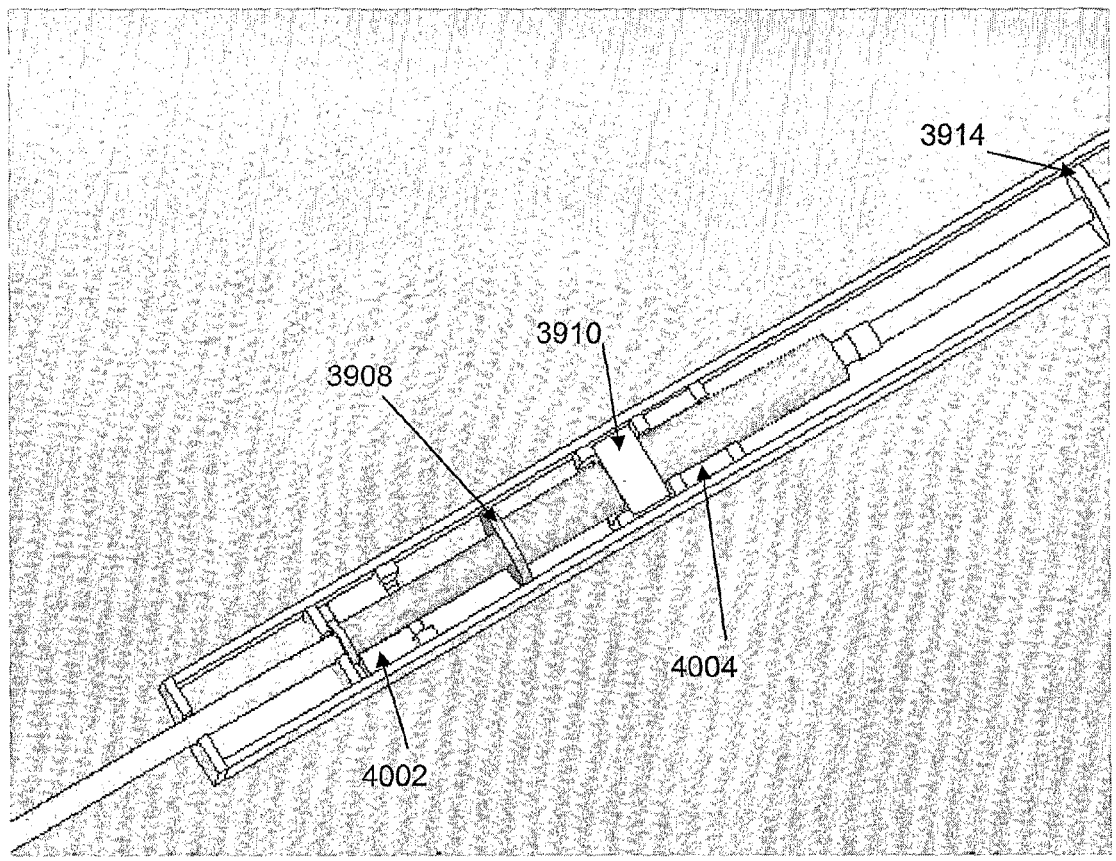

FIG. 40 shows a closer view of the assembly 3900. In addition to the cannula gear 3908, the cannula support 3910 and the stylet gear 3914, FIG. 40 shows a cannula stopper 4002 and a half nut 4004.

Figure 41:
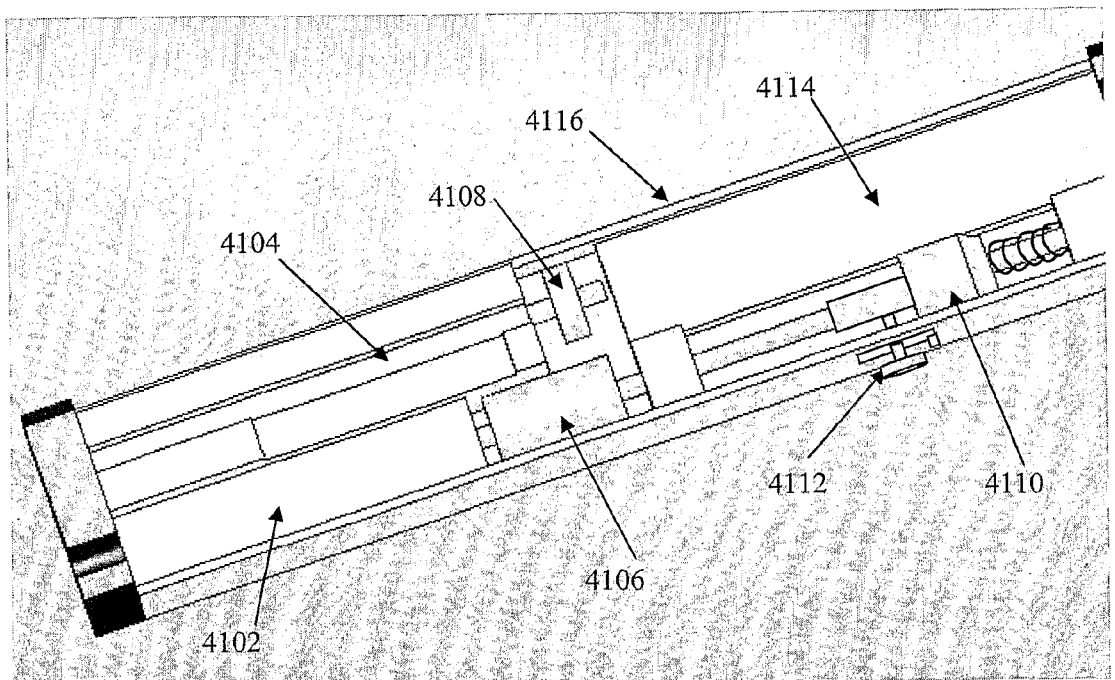

FIG. 41 shows the source of motive power for rotating the needle and driving the syringe. A first motor 4102 and a second motor 4104 transmit power through a first gear 4106 and a second gear 4108 respectively. The power from the first gear 4106 is in turn transmitted through a third gear 4110, which may be engaged or disengaged by pressing a button and mechanism 4112. Also provided are a controller, a battery and optionally also other circuitry 4114. The use of two motors and their associated gears allows the cannula and the stylet to be rotated together or separately under control of the operator. All the said motors, controller, battery, mechanisms and gears are enclosed in a housing 4116

Figure 42:
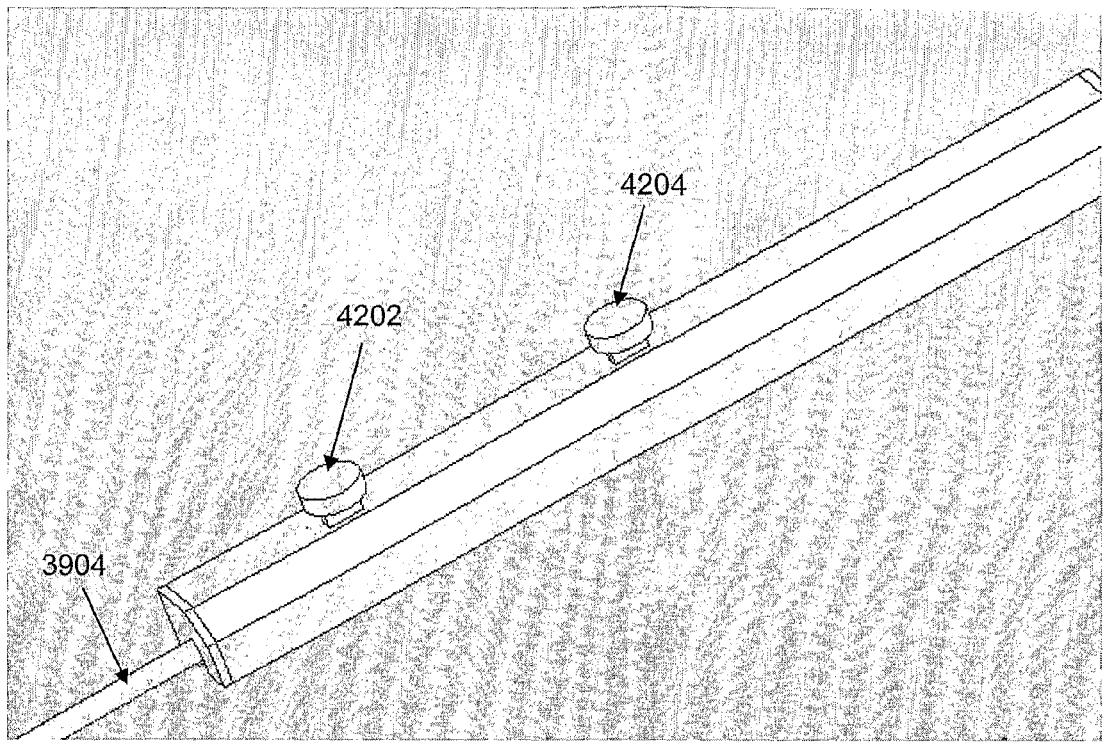

FIG. 42 shows an exterior view of the assembly 3900. Shown are two buttons 4202, 4204 for actuation by the operator to control operation of the assembly.

Figure 43:
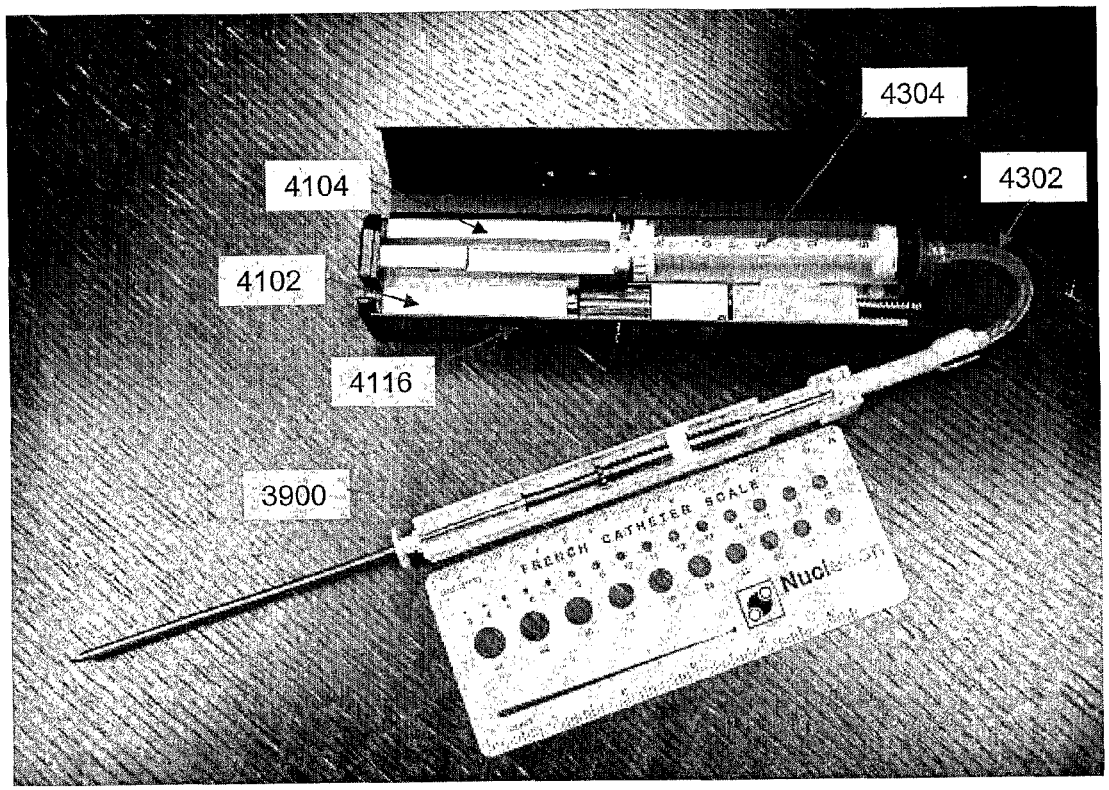

FIG. 43 shows the assembly 3900 connected to the source of motive power 4102 and 4104, and housing 4116. The two are connected by a flexible member 4302 which not only transmits motive power, but also allows the aspiration of tissues taken for biopsy into a cylinder 4304. Of course, the configuration could vary to suit the needs of any particular technique for biopsy, brachytherapy, tumor excision (such as lumpectomy) or the like.

The needle could be implemented as a coring needle with a cutting mechanism for systematic excision of cancerous tissue via motorized translation and rotation of such a needle, which can be done under the guidance of an imaging system such as ultrasound or MRI. Thus, the natural state of the cell histology can be preserved, especially around the margin of the excision.

Although two preferred embodiments of the present invention have been described, it will be recognized that numerous changes and variations can be made. For example, in either the first or the second preferred embodiment, or a device implementing both of the preferred embodiments, brachytherapy seeds can be replaced with any therapeutic or diagnostic capsules, such as chemotherapy drugs, virus, antibodies, heating rods, and other similar current or future therapeutic or diagnostic capsules. One particular example of such a therapeutic or diagnostic capsule is a sensor which is introduced interstitially through a needle to detect tumor nodules. Moreover, the number of degrees of freedom in both the robot and the passive platform is variable, as is whether the cart is lockable. Therefore, the scope of the present invention is intended to be defined only by the appended claims.

What is claimed is:

1. An automated system for delivery of therapeutic or diagnostic capsules to a required location of a patient's body, the system comprising:
   a needling mechanism which includes a cannula, a stylet, a support component, driving stages for the cannula and stylet, and a driving and motion transmission mechanism for cannula translation movement, stylet translation movement, and cannula rotation, wherein the driving and transmission mechanism is configured to rotate the cannula during insertion of the cannula in the patient's body, and wherein the needling mechanism pushes the therapeutic or diagnostic capsules into the patient's body to the required location;
   a robot for supporting the needling mechanism and moving the needling mechanism along x and y directions to provide a puncture area in the patient's body to implement a cannula insertion and capsule delivery plan, the robot including a side board;
   a passive platform for initial positioning and posturing of the needling mechanism and the robot; and
   a manual take over structure including a shaft and a knob, the shaft connecting the support component of the needling mechanism to the side board of the robot, wherein when the knob is removed from the manual take over structure, the needling mechanism is manually operable.

2. The system as in claim 1, wherein the needling mechanism comprises:
   a working status feedback system including encoders and force sensors, which provide feedback for automatic control and emergency cases;
   a therapeutic or diagnostic capsule cartridge holding mechanism; and
   an insulation and sterilization system for components which will be touched by a loading and unloading mechanism for loading and unloading components which need to be changed before or during operation of the automated system.

3. The system as in claim 2, wherein the therapeutic or diagnostic capsule cartridge holding mechanism includes a cartridge holder mounting on the cannula driving stage to accommodate a therapeutic or diagnostic capsule cartridge; the therapeutic or diagnostic capsule cartridge is arranged at a top position of said system; and the therapeutic or diagnostic capsule cartridge holding mechanism is arranged at a bottom position, so that the therapeutic or diagnostic capsule cartridge can be hidden inside the system to reduce a height of the system.

4. The system as in claim 3, wherein the therapeutic or diagnostic capsule cartridge is positioned by a spring plunger and tightened by a tightening knob for loading and unloading.

5. The system as in claim 4, wherein the therapeutic or diagnostic capsule cartridge is positioned and fixed by two plungers which are mounted on a side position of the cartridge holder to restrain the therapeutic or diagnostic capsule cartridge in position while working and to prevent the therapeutic or diagnostic capsule cartridge from dropping.

6. The system as in claim 2, wherein: the insulation and sterilization mechanism comprises a stylet sterilizer which is a round hollow column with a long slot in an outside surface, and the stylet when disposed in the stylet sterilizer is restrained against axial movement by a plunger which is at a position of the long slot.

7. The system as in claim 2, wherein the insulation and sterilization mechanism comprises a cannula sterilizer which is located in front of the cartridge holder and also is used as a cannula holder and force transmitter; and wherein the cannula sterilizer insulates the cannula and therapeutic or diagnostic capsules from cannula rotation drive gears which are just outside the cannula.

8. The system as in claim 7, wherein said cannula sterilizer has a larger diameter at one end than at the other end and has a larger hole at said one end to allow the a head of the cannula to be pushed in; and wherein at least one plunger is used to fix the cannula to rotate together with the sterilizer.

9. The system as in claim 8, wherein said at least one plunge comprises two plungers.

10. The system as in claim 9, wherein the head of the cannula is a flat plane in which one positioning hole is made in each side, and wherein the positioning holes fit the two plungers to achieve accurate positioning and fixing.

11. The system as in claim 7, wherein the cannula sterilizer is blocked by a plunger along an axial direction of the cannula sterilizer, and wherein said cannula sterilizer also acts on a force sensor, by which a cannula axial force is transferred to the force sensor.

12. The system as in claim 7, wherein the cannula sterilizer comprises a front end support sterilizer which is used to insulate the cannula and a front support component; wherein the cannula sterilizer has a screw shape for easy operation by a human hand; and wherein a round small groove is made in a journal position in the cannula sterilizer to accommodate a plunger.

13. The system as in claim 1, wherein the cannula rotation while inserting is transmitted by a group of small spur gears supported by a motor bracket.

14. The system as in claim 1, wherein the cannula translation movement, stylet translation movement and cannula rotation are all driven by motors coupled to ball screws.

15. The system as in claim 14, wherein said motors are selected from the group consisting of DC motors, AC motors and stepper motors.

16. The system as in claim 14, wherein two optical encoders are installed in back sides of the motors for driving the driving stages for the cannula and the stylet.

17. The system as in claim 14, wherein the motors are coupled to the ball screws by couplings.

18. The system as in claim 17, wherein said couplings include shaft direct connection couplings.

19. The system of claim 17, wherein the motors, couplings, and ball screws are in one line.

20. The system as in claim 14, wherein the motors are perpendicular to the ball screws in which motion transmission is by bevel gears.

21. The system of claim 14, wherein the motors are arranged off the ball screws by a distance and parallel in which motion transmission is by gears.

22. The system of claim 14, wherein two of the motors are for driving the ball screws and are connected with two encoders for detecting working status including rotation angle, rotation speed, and other related information.

23. The system as in claim 22, wherein the encoders include optical encoders or magnetic encoders.

24. The system as in claim 1, wherein: two z-direction force sensors are installed in back ends of the sty let and the cannula for detecting axial forces on the stylet and the cannula.

25. The system as in claim 24, wherein: a force transfer link is used for transmitting the axial force on the cannula to a position of one of the z-direction force sensors; the link is fixed in one side to the sensor by a screw which can also adjust a pre loading status of the sensor; another screw is mounted in the link and an end of said another screw touches a tip of the sensor; and said another screw also functions as an adjustment component of an angle between the link and the sensor which is a contact position of the link and a cannula sterilizer.

26. The system as in claim 24, wherein said z-direction force sensors include load cell or other single direction force sensors.

27. The system as in claim 26, further comprising an x-y force sensor for detecting a bending side on the cannula.

28. The system as in claim 27, wherein said x-y force sensor includes a 6-axis force sensor.

29. The system as in claim 1, further comprising an ultrasound probe and an ultrasound prove driver for translation and rotation of the ultrasound probe for translational scan and sagittal scan, wherein the ultrasound probe driver supports and drives the ultrasound probe for imaging or treatment of a prostate or other internal organs by transrectal method, the ultrasound probe driver comprising:
a support mechanism to support the ultrasound probe;
a support for supporting the ultrasound probe by holding or clamping the ultrasound probe so that accurate positioning and stable grasping can be obtained; and
a driving mechanism for driving the ultrasound probe to obtain translation and rotation motions to achieve longitudinal and sagittal scanning simultaneously or separately, wherein the translation motion or the rotation motion is performed continuously and without step, and the probe can stop and stay at any distance and any degree.

30. The system as in claim 29, wherein the translation motion is achieved by a ball screw transmission by which a rotation motion from a source of motive power is transferred to the translation motion.

31. The system as in claim 29, wherein the translation is achieved by a lead screw transmission.

32. The system as in claim 29, wherein the rotation motion is achieved by a ball spline.

33. The system as in claim 29, wherein the rotation motion of the ultrasound probe is achieved by a guide key for motion transmission from a moving stage.

34. The system as in claim 33, wherein the moving stage is supported by two guide rods arranged in left and right sagittal sides along a longitudinal axis, and wherein bushings are used to form a slide pair, whereby a compact guidance structure can be obtained.

35. The system as in claim 33, wherein the moving stage includes guide rails which can also be used as linear motion guidance.

36. The system as in claim 29, wherein the support for supporting the ultrasound probe is a half-ring bearing which comprises a static part and a rotation part with a shape of a half ring, and wherein said half-ring bearing further comprises a plurality of cam followers which are arranged circularly.

37. The system as in claim 36, wherein the plurality of cam followers comprises 6 to 100 cam followers.

38. The system as in claim 36, wherein the static part and the rotation part of the half-ring bearing are both half rings, whereby the ultrasound probe can be put into its holding position sidewise.

39. The system as in claim 36, wherein a home position of rotation motion of the ultrasound probe is determined by using one static dead block in a clamp frame and two rotational dead blocks in the rotation part of the half-ring bearing.

40. The system as in claim 39, wherein a limitation angle includes any value from 0 degree to 180 degree.

41. The system as in claim 36, wherein the ultrasound probe is positioned along its axial direction by a positioning piece mounted on a back side of the half-ring bearing in its end surface.

42. The system as in claim 29, wherein rotational motion is transmitted to the ultrasound probe by use of a gearing transmission.

43. The system as in claim 29, further comprising a clamp for clamping the ultrasound probe, the clamp comprising two opposite jaws with axial working length, wherein said jaws are driven by a thread shaft with reverse directional thread on two sides; and wherein once the thread shaft is turned by at least one tightening knob, the clamp jaws are driven to move closer together or farther apart to achieve clamping or releasing movements.

44. The system as in claim 43, wherein the clamp comprises two of said tightening knobs.

45. The system as in claim 43, wherein said jaws are supported and guided by two guide rods.

46. The system as in claim 43, wherein said jaws comprise linear motions components selected from the group consisting of guide rails, ball bearings, and bushings.

47. The system as in claim 43, wherein each jaw comprises, on a gripping side, a jaw pad made by high friction material with plastic probe surface, said jaw pad having the same sectional contour with the ultrasound probe.

48. The system as in claim 47, wherein said jaw pad is changeable to accommodate ultrasound probes of different sizes.

49. The system as in claim 29, wherein the driving mechanism for driving the ultrasound probe has a motorized driving mode and a manual driving mode which can work separately or simultaneously, wherein both of said two driving modes can drive the ultrasound probe move or rotate continuously, and can stop at any travel position or rotation angle.

50. The system as in claim 49, wherein the driving mechanism for driving the ultrasound probe comprises drive motors for the motorized mode, and wherein the drive motors are selected from the group consisting of DC motors, brush less DC motors, AC motors, and control and non-control motors with or without gearboxes.

51. The system as in claim 50, wherein the driving mechanism for driving the ultrasound probe comprises clutches for switching between the motorized mode and the manual mode is accomplished by two clutches, wherein the clutches connect the drive motors to a ball screw shaft and a ball spline shaft respectively.

52. The system as in claim 51, wherein said clutches are taken from the group consisting of electric control clutches and mechanical control clutches.

53. The system as in claim 51, wherein the driving mechanism for driving the ultrasound probe further comprises motion feedback sensors which are directly connected to at least one of the ball screw shaft and the ball spline shaft.

54. The system as in claim 53, wherein said encoders are hollow in structure to allow the ball screw shaft or ball spline shaft to pass through.

55. The system as in claim 49, wherein the driving mechanism for driving the ultrasound probe further comprises, for the manual mode, a drive knob assembly and a bevel gearing which transmit motion to a ball screw shaft and a ball spline shaft respectively, wherein the drive knob assembly is movable in an out of an engaging position manually.

56. The system as in claim 55, wherein the engaging position is maintained by turning a hollow shaft with four detents in an outside end into a locking position of a hook component.

57. The system as in claim 55, wherein the driving mechanism for driving the ultrasound probe further comprises an electric clutch and an electric switch to control the electric clutch to disconnect the motorized mode when working in manual mode to avoid a conflict between the two motion modes.

58. The system as in claim 55, wherein bevel gearings are used to transmit motion from the drive knob assembly to the ball screw and ball spline shafts.

59. The system as in claim 29, wherein the driving mechanism for driving the ultrasound probe operates only in motorized mode, without a manual mode.

60. The system as in claim 29, wherein the driving mechanism for driving the ultrasound probe operates only in manual mode, without a motorized mode.

61. The system as in claim 1, further comprising a front support frame, two stabilization needle guidance structures, and a commercial template for guiding brachytherapy needles.

62. The system as in claim 61, wherein a connection between the front support frame and the commercial template is by two round columns with two round holes by clearance fit.

63. The system as in claim 61, wherein the stabilization guidance structures have two degree of freedom, which can adjust angles around X axis and Y axis of stabilization needles.

64. The system as in claim 63, wherein the stabilization guidance structures are adjusted in the two degrees of freedom by manual operation, and further comprising rotation angle scales for obtaining an accurate angle setup.

65. The system as in claim 1, further comprising an angulations structure between the needling mechanism and the robot, for fixed angle adjustment of the needling mechanism.

66. The system as in claim 65, wherein the angulations structure includes two shafts, two screw knobs and a long circular groove in one connection board to allow the shafts to move relative to each other to achieve the angulations.

67. The system as in claim 1, wherein the manual take over structure comprises means for taking out two knobs to allow the needling mechanism to drop down.

68. The system as in claim 1, wherein the robot includes two motors, two ball screw transmissions, and guide rails.

69. The system as in claim 1, wherein the robot has a hanging up structure pattern which is arranged in a side place and below the ultrasound probe driver, for maximizing compactness and easy access to the ultrasound probe.

70. The system as in claim 1, wherein the passive platform has three linear joints and two revolute joints, so that up-down, left-right, forward-backward movements, pitch and yaw rotations are provided.

71. The system as in claim 70, wherein the five joints in the passive platform are self-locked by a worm gear transmission and a lead screw transmission that can stay at any position firmly.

72. The system as in claim 1, wherein the passive platform has two linear joints and two revolute joints, so that left-right, forward-backward movements, pitch and yaw rotations are.

73. The system as in claim 72, wherein both rotation joints in the passive platform use worm gear transmissions.

74. The system as in claim 72, wherein all the translation joints use lead screw transmissions.

75. The system as in claim 1, further comprising a cart, wherein the cart has one lock pedal which can fix the cart firmly on the ground, and one release pedal to go back to a status of wheel support.

76. The system as in claim 75, wherein the cart is supported on four feet which stretch out from the wheel base and stand on the ground.

77. The system as in claim 76, wherein the support feet are driven by a wedge with self-lock function.

78. The system as in claim 77, wherein said wedges are driven by link mechanism which are located in the bottom of the cart, and the link is driven by the lock pedal and release pedal.

79. The system as in claim 1, wherein the cannula is a hollow needle having a longitudinal axis, and wherein the system further comprises a motor for cannula rotation coupled to said needle, wherein said motor, when activated, is capable of rotating said needle around its longitudinal axis.

80. The system as in claim 79, wherein the motor is coupled to the needle by a gearing mechanism.

81. The system as in claim 79, wherein the motor and part of the needle are contained in a housing.

82. The system as in claim 79, wherein the motor contains a switch for activating and deactivating the motor.

83. The system as in claim 79, further comprising a controller for adjusting the rotational speed of the needle when the motor is activated.

84. The system as in claim 79, wherein the needle and the stylet are rotatable independently of each other.

85. The system as in claim 79, further comprising a device for removing tissue from the patient through the hollow needle.

86. The system as in claim 1, wherein the robot is a 2DOF robot.

87. The system as in claim 1, wherein the passive platform is a 5DOF passive platform.

88. The system as in claim 1, further comprising a cart, wherein the cart is lockable.

89. The automated system of claim 1, further comprising an ultrasound probe, and wherein the manual take over structure further comprises a switch for stopping a movement of the ultrasound probe when a manual take over of the movement of the ultrasound probe is desired.

90. The automated system of claim 1, further comprising a motor for rotating the cannula.

91. The automated system of claim 1, wherein the needling mechanism pushes the therapeutic or diagnostic capsules into the patient's body to the required location with insertion force detection.

92. The automated system of claim 1, wherein the needling mechanism pushes the therapeutic or diagnostic capsules into the patient's body to the required location with bending force detection.

93. The automated system of claim 1, wherein the passive platform realizes up-down, left-right and forward-backward movements, and pitch and yaw rotations.

94. The automated system of claim 1, further comprising a cart for supporting a remainder of the system.

95. The automated system of claim 1, wherein the needling mechanism angles the needles for avoidance of pubic arch interference.

96. The automated system of claim 1, wherein the needling mechanism stabilizes the prostate.

97. The automated system of claim 1, wherein the needling mechanism allows the operator to adjust needle position.

98. An automated system for delivery of therapeutic or diagnostic capsules to a required location of a patient's body, the system comprising:
   a needling mechanism which includes a cannula, a stylet, a support component, driving stages for the cannula and stylet, and a driving and motion transmission mechanism for cannula translation movement, stylet translation movement, and cannula rotation, wherein the needling mechanism pushes the therapeutic or diagnostic capsules into the patient's body to the required location;
   a robot for supporting the needling mechanism and automatically moving the needling mechanism along x and y directions to provide a puncture area in the patient's body to implement a cannula insertion and capsule delivery plan, the robot including a side board;
   a passive platform for initial positioning and posturing of the needling mechanism and the robot; and
   a manual take over structure including a shaft and a knob, the shaft connecting the support component of the needling mechanism to the side board of the robot, wherein when the knob is removed from the manual take over structure, the needling mechanism is manually operable.

\* \* \* \* \*